(12) United States Patent
Orlando et al.

(10) Patent No.: US 7,538,092 B2
(45) Date of Patent: May 26, 2009

(54) PHARMACEUTICALLY ACTIVE OLIGOSACCHARIDE CONJUGATES

(75) Inventors: Michele Orlando, Giessen (DE); Jurgen Hemberger, Aschaffenburg (DE); Jeanne Delbos-Krampe, Marburg (DE)

(73) Assignee: Fresenius Kabi Deutschland GmbH, Bad Homburg v.d.H. (DE)

( * ) Notice: Subject to any disclaimer, the term of this patent is extended or adjusted under 35 U.S.C. 154(b) by 137 days.

(21) Appl. No.: 10/530,849

(22) PCT Filed: Oct. 8, 2003

(86) PCT No.: PCT/EP03/11129

§ 371 (c)(1),
(2), (4) Date: Jan. 19, 2006

(87) PCT Pub. No.: WO2004/032971

PCT Pub. Date: Apr. 22, 2004

(65) Prior Publication Data

US 2006/0100163 A1 May 11, 2006

(30) Foreign Application Priority Data

Oct. 8, 2002 (DE) .......................... 202 15 415 U
Apr. 8, 2003 (EP) ............................... 03008177

(51) Int. Cl.
*A01N 43/04* (2006.01)
*A61K 31/70* (2006.01)

(52) U.S. Cl. .................. 514/25; 536/18.5; 536/18.6

(58) Field of Classification Search ............... None
See application file for complete search history.

(56) References Cited

U.S. PATENT DOCUMENTS

| | | | |
|---|---|---|---|
| 3,191,291 A | 6/1965 | Maier | |
| 4,064,118 A | 12/1977 | Wong | |
| 4,125,492 A | 11/1978 | Cuatrecasas et al. | |
| 4,179,337 A | 12/1979 | Davis et al. | |
| 4,261,973 A | 4/1981 | Lee et al. | |
| 4,412,989 A | 11/1983 | Iwashita et al. | |
| 4,667,016 A | 5/1987 | Lai et al. | |
| 4,703,008 A | 10/1987 | Lin | |
| 4,766,106 A | 8/1988 | Katre et al. | |
| 4,847,325 A | 7/1989 | Shadle et al. | |
| 4,863,964 A | 9/1989 | Hedlund et al. | |
| 4,900,780 A | 2/1990 | Cerny | |
| 4,904,584 A | 2/1990 | Shaw | |
| 4,952,496 A | 8/1990 | Studier et al. | |
| 5,068,321 A | 11/1991 | Buysch et al. | |
| 5,079,337 A | 1/1992 | Leonard et al. | |
| 5,214,132 A | 5/1993 | Kuga et al. | |
| 5,217,998 A | 6/1993 | Hedlund et al. | |
| 5,218,092 A | 6/1993 | Sasaki et al. | |
| 5,218,108 A | 6/1993 | Sommermeyer et al. | |
| 5,281,698 A | 1/1994 | Nitecki | |
| 5,362,853 A | 11/1994 | Kuga et al. | |
| 5,470,843 A | 11/1995 | Stahl et al. | |
| 5,484,903 A | 1/1996 | Szablikowski et al. | |
| 5,543,332 A | 8/1996 | Lihme et al. | |
| 5,581,476 A | 12/1996 | Osslund | |
| 5,622,718 A | 4/1997 | Al-Shamkhani et al. | |
| 5,723,589 A * | 3/1998 | Miljkovic et al. | .......... 536/1.11 |
| 5,876,980 A | 3/1999 | DeFrees et al. | |
| 5,880,270 A | 3/1999 | Berninger et al. | |
| 6,011,008 A | 1/2000 | Domb et al. | |
| 6,083,909 A | 7/2000 | Sommermeyer et al. | |
| 6,299,881 B1 | 10/2001 | Lees et al. | |
| 6,340,746 B1 | 1/2002 | Roberts et al. | |
| 6,500,930 B2 | 12/2002 | Adamson | |
| 6,555,660 B2 | 4/2003 | Nissen et al. | |
| 6,586,398 B1 | 7/2003 | Kinstler et al. | |
| 2004/0180858 A1 | 9/2004 | Sommermeyer | |
| 2005/0063943 A1 | 3/2005 | Sommermeyer et al. | |
| 2005/0238723 A1 | 10/2005 | Zander et al. | |
| 2006/0019877 A1 | 1/2006 | Conradt et al. | |
| 2006/0217293 A1 | 9/2006 | Orlando et al. | |

FOREIGN PATENT DOCUMENTS

CA 2 233 725 9/1999

(Continued)

OTHER PUBLICATIONS

Adamczyk and Fishpaugh, "A Solid Supported Synthesis of Thiol Esters," *Tetrahedron Lett.*, 1996, 37(25):4305-4308.

Aly et al., "Hemophilia A due to mutations that create new N-glycosylation sites," *Proc. Natl. Acad. Sci. USA*, 1992, 89:4933-4937.

Andersson et al., "Isolation and characterization of human factor VIII: Molecular forms in commercial factor VIII concentrate, cryoprecipitate, and plasma," *Proc. Natl. Acad. Sci. USA*, 1986, 83:2979-2983.

Armitage, "Emerging Applications of Recombinant Human Granulocyte-Macrophage Colony-Stimulating Factor," *Blood*, 1998, 92(12):4491-4508.

(Continued)

*Primary Examiner*—Patrick T Lewis
(74) *Attorney, Agent, or Firm*—Fish & Richardson P.C.

(57) ABSTRACT

The present invention relates to pharmaceutically active oligosaccharide conjugates having the formula: $(X-Y_m)_n-S$, wherein component X is a pharmaceutically active compound, Y is a bifunctional linker, and S is an oligosaccharide consisting of 1 to 20 saccharide units, n is equal or less than the number of the saccharide units in the oligosaccharide S, and m is, independent of n, 0 or 1. In addition, the present invention is directed to a process of preparing compounds of the present invention, comprising the step of coupling components X and S directly or indirectly by means of a bifunctional linker group. Furthermore, the present invention relates to the use of said pharmaceutically active oligosaccharide conjugates as a medicament as well as to pharmaceutical compositions, freeze-dried pharmaceutical compositions, and a kit, all of which comprise at least one of said pharmaceutically active oligosaccharide conjugates.

42 Claims, 1 Drawing Sheet

FOREIGN PATENT DOCUMENTS

Figure 1:
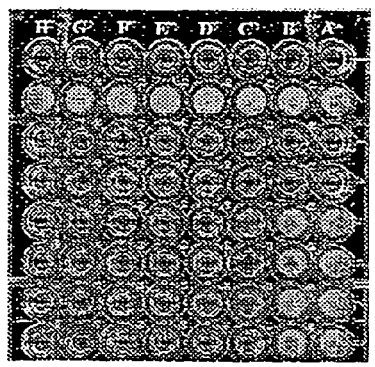

| | | |
|---|---|---|
| CA | 2 441 442 | 9/2003 |
| CA | 2 478 478 | 1/2004 |
| CA | 2 478 480 | 1/2004 |
| DE | 22 33 977 | 2/1973 |
| DE | 26 16 086 | 11/1977 |
| DE | 30 29 307 | 3/1982 |
| DE | 26 46 854 | 5/1989 |
| DE | 38 36 600 | 5/1990 |
| DE | 279 486 | 6/1990 |
| DE | 41 30 807 | 3/1993 |
| DE | 26 07 706 | 5/1993 |
| DE | 196 28 705 | 1/1998 |
| DE | 198 08 079 | 8/1999 |
| DE | 101 12 825 | 2/2002 |
| DE | 100 41 541 | 3/2002 |
| DE | 101 26 158 | 12/2002 |
| DE | 101 35 694 | 2/2003 |
| DE | 101 29 369 | 3/2003 |
| DE | 101 55 098 | 5/2003 |
| DE | 102 09 821 | 9/2003 |
| DE | 102 17 994 | 11/2003 |
| DE | 102 54 745 | 6/2004 |
| DE | 102 56 558 | 9/2004 |
| EP | 0 019 403 | 11/1980 |
| EP | 0 138 572 | 4/1985 |
| EP | 0 218 825 | 4/1987 |
| EP | 0 243 929 | 11/1987 |
| EP | 0 304 183 | 2/1989 |
| EP | 0 307 827 | 3/1989 |
| EP | 0 315 349 | 5/1989 |
| EP | 0 338 916 | 10/1989 |
| EP | 0 402 724 | 6/1990 |
| EP | 0 148 605 | 7/1990 |
| EP | 0 205 564 | 5/1991 |
| EP | 0 428 267 | 5/1991 |
| EP | 0 411 678 | 1/1992 |
| EP | 0 127 839 | 7/1992 |
| EP | 0 331 471 | 12/1992 |
| EP | 0 549 721 | 4/1994 |
| EP | 0 605 963 | 7/1994 |
| EP | 0 609 968 | 8/1994 |
| EP | 0 342 557 | 11/1994 |
| EP | 0 640 619 | 3/1995 |
| EP | 0 646 130 | 4/1995 |
| EP | 0 418 523 | 6/1995 |
| EP | 0 668 351 | 8/1995 |
| EP | 0 809 996 | 5/1996 |
| EP | 1 230 935 | 8/2002 |
| EP | 1 400 533 | 9/2002 |
| EP | 1 398 322 | 9/2003 |
| EP | 1 398 327 | 9/2003 |
| EP | 1 398 328 | 9/2003 |
| EP | 1 424 086 | 6/2004 |
| FR | 2 378 094 | 8/1978 |
| GB | 1 419 080 | 12/1975 |
| GB | 1 549 246 | 10/1976 |
| WO | WO 90/07939 | 7/1990 |
| WO | WO 90/15628 | 12/1990 |
| WO | WO 93/23062 | 11/1993 |
| WO | WO 94/01483 | 1/1994 |
| WO | WO 94/05332 | 3/1994 |
| WO | WO 94/07536 | 4/1994 |
| WO | WO 94/13697 | 6/1994 |
| WO | WO 94/28024 | 12/1994 |
| WO | WO 94/29370 | 12/1994 |
| WO | WO 95/06058 | 3/1995 |
| WO | WO 95/13090 | 5/1995 |
| WO | WO 96/11953 | 4/1996 |
| WO | WO 96/19242 | 6/1996 |
| WO | WO 96/40662 | 12/1996 |
| WO | WO 96/41813 | 12/1996 |
| WO | WO 97/21452 | 6/1997 |
| WO | WO 97/30148 | 8/1997 |
| WO | WO 97/33552 | 9/1997 |
| WO | WO 97/38727 | 10/1997 |
| WO | WO 98/01158 | 1/1998 |
| WO | WO 98/08856 | 3/1998 |
| WO | WO 98/20905 | 5/1998 |
| WO | WO 98/32466 | 7/1998 |
| WO | WO 98/56424 | 12/1998 |
| WO | WO 99/07719 | 2/1999 |
| WO | WO 99/49897 | 10/1999 |
| WO | WO 00/78355 | 12/2000 |
| WO | WO 01/70272 | 9/2001 |
| WO | WO 02/09766 | 2/2002 |
| WO | WO 02/20033 | 3/2002 |
| WO | WO 02/40057 | 5/2002 |
| WO | WO 02/80979 | 10/2002 |
| WO | WO 03/000738 | 1/2003 |
| WO | WO 03/031464 | 4/2003 |
| WO | WO 03/031581 | 4/2003 |
| WO | WO 03/059246 | 7/2003 |
| WO | WO03/070772 | 8/2003 |
| WO | WO 03/074087 | 9/2003 |
| WO | WO 03/074088 | 9/2003 |
| WO | WO 2004/009082 | 1/2004 |
| WO | WO 2004/024761 | 3/2004 |
| WO | WO 2004/024776 | 3/2004 |
| WO | WO 2004/024777 | 3/2004 |
| WO | WO 2004/030701 | 4/2004 |
| WO | WO 2004/033651 | 4/2004 |
| WO | WO 2004/050710 | 6/2004 |
| WO | WO 2004/065425 | 8/2004 |
| WO | WO 2005/014024 | 2/2005 |
| WO | WO 2005/014035 | 2/2005 |
| WO | WO 2005/014050 | 2/2005 |
| WO | WO 2005/014655 | 2/2005 |
| WO | WO 2005/074993 | 8/2005 |
| WO | WO 2005/092390 | 10/2005 |
| WO | WO 2006/0108052 | 10/2006 |

OTHER PUBLICATIONS

Balland et al., "Characterisation of two differently processed forms of human recombinant factor IX synthesised in CHO cells transformed with a polycistronic vector," *Eur. J. Biochem.*, 1988, 172(3):565-572.

Bauer and Rosenberg, "Role of Antithrombin III as a Regulator of In Vivo Coagulation," *Semin. Hematol.*, 1991, 28:10-18.

Berg et al., "Engineering the proteolytic specificity of activated protein C improves its pharmacological properties," *Proc. Natl. Acad. Sci. USA*, 2003, 100(8):4423-4428.

Bhattacharyya et al., "Recombinant Factor VIII for Haemophilia An Overview of Production Technologies," *CRIPS*, 2003, 4(3):2-8.

Björk and Danielsson, "Antithrombin and related inhibitors of coagulation proteinases," *Proteinase Inhibitors*, 1986, Chapter 17, pp. 489-513.

Boorsma et al., "Bioprocess Applications of a Sindbis Virus-Based Temperature-Inducible Expression System," *Biotech. Bioeng.*, 2002, 79(6): 602-609.

Carrell et al., "Human $\alpha_1$-antitrypsin: carbohydrate attachment and sequence homology," *FEBS Lett.*, 1981, 135(2):301-303.

Carrell et al., "Structural Mobility of Antithrombin and its Modulation by Heparin," *Thromb. Haemost.*, 1997, 78:516-519.

Carver et al., "Expression of human $\alpha$1 antitrypsin in transgenic sheep," *Cytotechnology*, 1992, 9:77-84.

Castillo et al., "Sensitive Substrates for Human Leukocyte and Porcine Pancreatic Elastase: A Study of the Merits of Various Chromophoric and Fluorogenic Leaving Groups in Assays for Serine Proteases," *Anal. Biochem.*, 1979, 99:53-64.

Cebon et al., "Granulocyte-Macrophage Colony Stimulating Factor from Human Lymphocytes. The effect of glycosylation on receptor binding and biological activity," *J. Biol. Chem.*, 1990, 265(8):4483-4491.

Chamow and Ashkenazi, *Antibody Fusion Proteins*, 1999, Wiley & Sons, Inc. (TOC Only).

Chan et al., "Preparation of O-esters from the corresponding thiol esters: *tert*-butyl cyclohexanecarboxylate," *Organic Syntheses. Coll.*, 1990, 7:87-93.

Chen et al., "Purification of $\alpha_1$ Proteinase Inhibitor from Human Plasma Fraction IV-1 by Ion Exchange Chromatography," *Vox Sang*, 1998, 74:232-241.

Choay et al., "Structural studies on a biologically active hexasaccharide obtained from heparin," *Ann. NY Acad. Sci.*, 1981, 370:644-649.

Choay et al., "Structure-activity relationship in heparin: a synthetic pentasaccharide with high affinity for antithrombin III and eliciting high anti-factor Xa activity," *Biochem. Biophys. Res. Commun.*, 1983, 116(2):492-499.

Colman, "Production of therapeutic proteins in the milk of transgenic livestock," *Biochem. Soc. Symp.*, 1998, 63:141-147.

Conradt et al., "Expression of Human Interleukin-2 in Recombinant Baby Hamster Kidney, Ltk⁻, and Chinese Hamster Ovary Cells. Structure of O-linked carbohydrate chains and their location within the polypeptide," *J. Biol. Chem.*, 1989, 264(29):17368-17373.

Corey and Clark, "A new method for the synthesis of 2-pyridinethiol carboxylic esters," *Tetrahedron Lett.*, 1979, 31:2875-2878.

de Koning et al., "An approach to the synthesis of peptide-PNA-peptide conjugates via native ligation," *Tetrahedron Lett.*, 2002, 43(45): 8173-8176.

Denzlinger et al., "Differential Activation of the Endogenous Leukotriene Biosynthesis by Two Different Preparations of Granulocyte-Macrophage Colony-Stimulating Factor in Healthy Volunteers," *Blood*, 1993, 81(8):2007-2013.

Donahue et al., "Effects of N-linked Carbohydrates on the In Vivo Properties of Human GM-CSF," *Cold Spring Harbor Symp. Quant. Biol.*, 1986, 51:685-692.

Edmunds et al., "Transgenically Produced Human Antithrombin: Structural and Functional Comparison to Human Plasma-Derived Antithrombin," *Blood*, 1998, 91(12):4561-4571.

Ernst et al. (eds.), *Carbohydrates in Chemistry and Biology*, 2000, Part I, vol. 1-2, Whiley-VCH Weinheim (TOC only).

European Pharmacopoeia, 2001, 911-917.

Forno et al., "N- and O-linked carbohydrates and glycosylation site occupancy in recombinant human granulocyte-macrophage colony-stimulating factor secreted by a Chinese hamster ovary cell line," *Eur. J. Biochem.*, 2004, 271(5):907-919.

Franzen and Svensson, "Stuctural Studies on the Carbohydrate Portion of Human Antithrombin III," *J. Biol. Chem.*, 1980, 255(11):5090-5093.

Fujiki et al., "Studies on the disulfide bonds in human pituitary follicle-stimulating hormone," *Biochim. Biophys. Acta*, 1980, 624: 428-435.

Goldstein and Gelb, "An alternate preparation of thioester resin linkers for solid-phase synthesis of peptide C-terminal thioacids," *Tetrahedron Lett.*, 2000, 41(16):2797-2800.

Goronzy et al., "T-Cell Derived Lymphokines as Regulators of Chronic Inflammation: Potential Targets for Immunomodulation?" *Am. J. Ther.*, 1996, 3(2):109-114.

Gribben et al., "Development of antibodies to unprotected glycosylation sites on recombinant GM-CSF," *Lancet*, 1990, 335:434-437.

Harris et al., "Pegylation. A novel process for modifying pharmacokinetics," *Clin. Pharmacokinet*, 2001, 40(7): 539-551.

He et al., "A simplified system for generating recombinant adenoviruses," *Proc. Natl. Acad. Sci. USA*, 1998, 95:2509-2514.

Hodges and Chan, "Locations of Oligosaccharide Chains in Human α1-Protease Inhibitor and Oligosaccharide Structures at Each Site," *Biochemistry*, 1982, 21:2805-2810.

Hodges et al., "Structure of the Oligosaccharide Chains in Human $\alpha_1$-Protease Inhibitor," *J. Biol. Chem.*, 1979, 254(17):8208-8212.

Hovgaard et al., "Clinical pharmacokinetic studies of a human haemopoietic growth factor, GM-CSF," *Eur. J. Clin. Inv.*, 1992, 22:45-49.

Hovinen et al., "Ethyl[2-deoxy-5-0-(4,4'-dimethoxytrityl)-α-and β-D-*erythro*-pentofuranosyl] acetates as versatile intermediates in nucleic acid chemistry," *Nucleosides Nucleotides*, 1999, 18:1263-1264.

Iakovenko et al., "Semi-synthetic Rab proteins as tools for studying intermolecular interactions," *FEBS Letters*, 2000, 468:155-158.

Ingenito et al., "Solid Phase Synthesis of Peptide C-Terminal Thioesters by Fmoc/*t*-Bu Chemmistry," *J. Am. Chem. Soc.*, 1999, 121:11369-11374.

Jaques et al., "N.M.R. spectroscopy and calcium binding of sialic acids: *N*-glycolylneuraminic acid and periodate-oxidized *N*-acetylneuraminic acid," *Carb. Res.*, 1980, 83:21-32.

Karpusas et al., The crystal structure of human interferon β at 2.2-Å resolution, *Proc. Natl. Acad. Sci. USA*, 1997, 94:11813-11818.

Kaufman et al., "Synthesis, Processing, and Secretion of Recombinant Human Factor VIII Expressed in Mammalian Cells," *J. Biol. Chem.*, 1988, 263(13):6352-6362.

Kaushansky et al., "Role of Carbohydrate in the Function of Human Granulocyte-Macrophage Colony-Stimulating Factor," *Biochemistry*, 1987, 26:4861-4867.

Keene et al., "Expression of Biologically Active Human Follitropin in Chinese Hamster Ovary Cells," *J. Biol. Chem.*, 1989, 264(9):4769-4775.

Kochendoerfer et al., "Design and Chemical Synthesis of a Homogeneous Polymer-Modified Erythropoiesis Protein," *Science*, 2003, 299(5608):884-887.

Kraehenbuhl et al., "Preparation and characterization of an immunoelectron microscope tracer consisting of a heme-octapeptide coupled to Fab," *J. Exp. Med.*, 1974, 139:208-223.

Lahiri et al., "Antithrombin-Heparin Cofactor: An Inhibitor of Plasma Kallikrein," *Arch. Biochem. Biophys.*, 1976, 175:737-747.

Lapthorn et al., "Crystal structure of human chorionic gonadotropin," *Nature*, 1994, 369:455-461.

Levy et al., "Recombinant Antithrombin: Production and Role in Cardiovascular Disorder," *Sem. Thromb. Hem.*, 2001, 27(4):405-416.

Li et al., "Direct preparation of peptide thioesters using an Fmoc solid-phase method," *Tetrahedron Lett.*, 1998, 39(47):8669-8672.

Lin et al., "L-Cysteine as a water-soluble cation scavenger in the removal of the 2,4,6-trimethoxybenzyl group from thiols," *Tetrahedron Lett.*, 2002, 43:4531-4533.

March, "Delocalized Chemical Bonding," *Adv. Org. Chem.*, 1992, 4th Edition, John Wiley and Sons, New York, Chapter 2 pp. 26-292.

Masamune et al., "A General, Selective Synthesis of Thiol Esters," *Can. J. Chem.*, 1975, 53:3693-3695.

Masamune et al., "Tylonolide Hemiacetal, the Aglycone of Tylosin, and Its Partial Synthesis," *J. Am. Chem. Soc.*, 1976, 98:7874-7875.

Masuda et al., "Synthesis and Anti-Influenza Evaluation of Orally Active Bicyclic Ether Derivatives Related to Zanamivir," *Bioorganic & Medicinal Chemistry Letters*, 2003, 13:669-673.

Mega et al., "Studies on the Oligosaccharide Chains of Human $\alpha_1$-Protease Inhibitor. I. Isolation of glycopeptides," *J. Biol. Chem*, 1980, 255(9):4053-4056.

Mega et al., "Studies on the Oligosaccharide Chains of Human $\alpha_1$-Protease Inhibitor. II. Structure of oligosaccharides," *J. Biol. Chem.*, 1980, 255(9):4057-4061.

Menache, "Antithrombin III: Introduction," *Semin. Hematol.*, 1991, 28:1-2.

Menache et al., "Antithrombin III: physiology, deficiency, and replacement therapy," *Transfusion*, 1992, 32:580-588.

Ming et al., "Interleukin 6 is the Principal Cytolytic T Lymphocyte Differentiation Factor for Thymocytes in Human Leukocyte Conditioned Medium," *J. Mol. Cell. Immunol.*, 1989, 4:203-212.

Moonen et al., "Increased biological activity of delycosylated recombinant human granulocyte/macrophage colony-stimulating factor produced by yeast or animal cells," *Proc. Natl. Acad. Sci. USA*, 1987, 84:4428-4431.

Mori et.al., "The Activation of Type 1 and Type 2 Plasminogen by Type I and Type II Tissue Plasminogen Activator," *J. Biol. Chem.*, 1995, 270(7):3261-3267.

Muir et al., "Expressed protein ligation: A general method for protein engineering," *Proc. Natl. Acad. Sci. USA*, 1998, 95:6705-6710.

Mukaiyama et al., "Peptide Synthesis *via* Oxidation-Reduction Condensation by the Use of Non-metallic Compound as a Mercaptan Scavenger," *Bull. Chem. Soc. Jpn.*, 1970, 43:1271.

Mumberg et al., "Regulatable promoters of *Saccharomyces cerevisiae*: comparison of transcriptional activity and their use for heterologous expression," *Nucl. Acids Res.*, 1994, 22(25):5767-5768.

Murano et al., "Some properties of antithrombin-III and its concentration in human plasma," *Thromb. Res.*, 1980, 18:259-262.

Ohta et al., "Usefulness of Glycopeptide Mapping by Liquid Chromatography/Mass Spectrometry in Comparability Assessment of Glycoprotein Products," *Biologicals*, 2002, 30(3):235-244.

Okamoto et al., "Purification and Characterization of Three Forms of Differently Glycosylated Recombinant Human Granulocyte-Macrophage Colony-Stimulating Factor," *Arch. Biochem. Biophys.*, 1991, 286(2):562-568.

Olson et al., "Role of the Antithrombin-binding Pentasaccharide in Heparin Acceleration of Antithrombin-Proteinase Reactions. Resolution of the antithrombin conformational change contribution to heparin rate enhancement," *J. Biol. Chem.*, 1992, 267(18):12528-12538.

Olson and Björk, "Predominant Contribution of Surface Approximation to the Mechanism of Heparin Acceleration of the Antithrombin-Thrombin Reaction. Elucidation from salt concentration effects," *J. Biol. Chem.*, 1991, 266(10):6353-6364.

Opal et al., "Antithrombin, heparin, and heparan sulfate," *Crit. Care Med.*, 2002, 30(5):S325-S331.

Pelter et al., "Synthesis of Thioesters by Reactions of Carboxylic Acids with Tris-(ethylthio)borane," *J. Am. Chem. Soc., Perkin Trans 1*, 1977, 1672-674.

Peterson, *The Physiological Inhibitions of Blood Coagulation and Fibrinolysis*, 1979, Elsevier/North-Holland Biomedical Press, p. 43.

Pike et al., "Heparin-dependent Modification of the Reactive Center Arginine of Antithrombin and Consequent Increase in Heparin Binding Affinity," *J. Biol. Chem.*, 1997, 272_32:19652-19655.

Ragnhammar et al., "Induction of Anti-Recombinant Human Granulocyte-Macrophage Colony-Stimulating Factor (*Escherichia coli*-Derived) Antibodies and Clinical Effects in Nonimmunocompromised Patients," *Blood*, 1994, 84(12):4078-4087.

Rapoport et al., "Protein transport across the eukaryotic endoplasmic reticulum and bacterial inner membranes," *Annu. Rev. Biochem.*, 1996, 65:271-303.

Reddy et al., "Use of peginterferon alfa-2a (40 KD) (Pegasys®) for the treatment of hepatitis C," *Advanced Drug Delivery Reviews*, 2002, 54:571-586.

Reischl (ed)., *Molecular Diagnosis of Infectious Diseases*, 1997, vol. 13, Totowa NJ, Humana Press Inc. (TOC Only).

Reidhaar-Olson et al., "Identification of Residues Critical to the Activity of Human Granulocyte Colony-Stimulating Factor," *Biochemistry*, 1996, 35:9034-9041.

Revoltella et al., "Natural and Therapy-Induced Anti-GM-CSF and Anti-G-CSF Antibodies in Human Serum," *Leukemia and Lymphoma*, 1997, 26:29-34.

Roemisch et al., "Antithrombin: a new look at the actions of a serine protease inhibitor," *Blood Coagul. Fibrinolysis*, 2002, 13:657-670.

Rosenberg, "Role of heparin and heparinlike molecules in thrombosis and atherosclerosis," *Fed. Proc.*, 1985, 44:404-409.

Rosenberg et al., "Antithrombin-III," *Rev. Hematol.*, 1986, 2:351-416.

Schlesinger, "Alphaviruses—vectors for the expression of heterologous genes," *Trends Biotech.*, 1993, 11:18-22.

Schröter et al., "Male-specific Modification of Human CD52," *J. Biol. Chem.*, 1999, 274(42):29862-29873.

Shin et al., "Fmoc-Based Synthesis of Peptide-αThioesters: Application to the Total Chemical Synthesis of a Glycoprotein by Native Chemical Ligation," *J. Am. Chem. Soc.*, 1999, 121:11684-11689.

Spellman et al., "Carbohydrate Structures of Human Tissue Plasminogen Activator Expressed in Chinese Hamster Ovary Cells," *J. Biol. Chem.*, 1989, 264(24):14100-14111.

Stetsenko and Gait, "Efficient Conjugation of Peptides to Oligonucleotides by Native Ligation," *J. Org. Chem.*, 2000, 65:4900-4908.

Stewart et al., "Identification of the Mechanism Responsible for the Increased Fibrin Specificity of TNK-Tissue Plasminogen Activator Relative to Tissue Plasminogen Activator," *J. Biol. Chem.*, 2000, 275(14):10112-10120.

Tam et al., "Peptide Synthesis Using Unprotected Peptides Through Orthogonal Coupling Methods," *Proc. Natl. Acad. Sci. USA*, 1995, 92:12485-12489.

Tebbutt, "Technology evaluation: transgenic α-1-antitrypsin (AAT), PPL Therapeutics," *Curr. Opin. Mol. Ther.*, 2000, 2(2):199-204.

Thim et al., "Amino Acid Sequence and Posttranslational Modification of Human Factor VII$_a$ from Plasma and Transfected Baby Hamster Kidney Cells," *Biochemistry*, 1988, 27:7785-7793.

Toole et al., "Molecular cloning of a cDNA encoding human antihaemophilic factor," *Nature*, 1984, 312:342-347.

Travis and Salvesen, "Human plasma proteinase inhibitors," *Ann. Rev. Biochem.*, 1983, 52:655-709.

Veronese et al., "Peptide and Protein PEGylation—A Review of Problems and Solutions," *Biomaterials*, 2001, 22(5):405-417.

Wadhwa et al., "Immunogenicity of Granulocyte-Macrophage Colony-Stimulating Factor (GM-CSF) Products in Patients Undergoing Combination Therapy with GM-CSF," *Clin. Cancer Res.*, 1999, 5:1351-1361.

Watanabe et al., "A facile synthesis of carboxylic thiol esters from carboxylic acids and thiols," *Chem. Lett.*, 1976, 741-742.

Weisshaar et al., "NMR investigations of the N-linked oligosaccharides at individual glycosylation sites of human lutropin," *Eur. J. Biochem.*, 1991, 195:257-268.

Wright et al., "High level expression of active human alpha-1-antitrypsin in the milk of transgenic sheep," *Biotechnology*, 1991, 9:830-834.

Yoshitake et al., "Nucleotide Sequence of the Gene for Human Factor IX (Antihemophilic factor B)," *Biochemistry*, 1985, 24:3736-3750.

Wong, Chemical Dictionary Entry Concerning Carbohydrates, *Chemistry of Protein Conjugation and Cross-Linking*, 1993, CRCS, Inc., 6 pages including English-language Abstract.

Frie, "Evaluating a Novel Method for Coupling of Low Molecular Hydroxyethylstarch with Model Compounds and Application of this Method to further Selected Proteins," Diploma Thesis dated Feb. 2, 1998, Diplomarbeit, Fachhochschule, Hamburg, Germany, 82 pages including English-language Abstraact.

Schmoll et al. (eds.), "Summary of Basics of Oncology and Current Therapeutic Approaches," *Compendium for Internistic Oncology*, 1996, Table of Contents with English Summary.

Sommermeyer et al., "Hydroxyethylstarch for Clinical Application: Physical and Chemical Characterisation," *Krankenhauspharmazie*, 1987, 8:271-278.

Staab, "New Methods in Preparatory Organic Chemistry IV. Synthesis using heterocyclic amides (azolides)," *Angew. Chem.*, 1962, 74(12):407-422.

Stille et al., "Atherosclerosis as Consequence of Chronic Infection by Chlamydia Pneumoniae," *Herz*, 1998, 23:185-192 (w/English summary).

Gaucher et al., "Stereospecific synthesis and characterization of aminoglycoside ligands from diethylenetriamine," *J. Organic Chem.*, 1999, 64:4012-4015.

Definition of dimethyl sulfoxide, the Merck Index, 2006, Merck & Co., 14th edition, accessed online http://themerckindex.cambridgesoft.com/TheMerckIndex/index.asp on Sep. 4, 2007.

Dieterich et al., "Hydroxyethyl Starch Antibodies in Humans: Incidence and Clinical Relevance," *Anesth. Analg.*, 1998, 86:1123-1126.

Sakai et al. "Synthesis and Physicochemical Characterization of a series of Hemoglobin-Based Oxygen Carriers: Objective Comparison between Cellular and Acellular Types," *Bioconjugate Chem.*, 2000, 11:56-64.

Guillaumie et al., "Immobilization of pectin fragments on solid supports: Novel coupling by thiazolidine formation," *Bioconjugate Chem.*, 2002, 13:285-294.

Liu et al., "Characterization of the structural and functional changes of hemoglobin in dimethyl sulfoxide by spectroscopic techniques," *Biochim. Biophys. Acta*, 1998, 138:53-60.

Okamoto et al., "A facile incorporation of the aldehyde function into DNA: 3-formylindole nucleoside as an aldehyde-containing universal nucleoside," *Tetrahedron Lett.*, 2002, 43:4581-4583.

Radomsky and Temeriusz, "Thiazolodine-4(R)-carboxylic acids derived from sugars: part I, C-2-epimerisation in aqueous solutions," *Carb. Res.*, 1989, 187:223-237.

Shao and Tam, "Unprotected peptides as building blocks for synthesis of peptide dendrimers with oxime, hydrazone and thiazolidine linkages," *J. Am. Chem. Soc.*, 1995, 117(14):3893-3899.

Yang et al., "Functional changes of carboxymethyl potato starch by conjugation with amino acids," *Biosci. Biotechnol. Biochem.*, 1995, 59(12):2203-2206.

Abuchowski and Davis, "Soluble Polymer-Enzyme Adducts," *Enzymes as Drugs*, 1981, Holcenberg and Rubberts (eds.), Chapter 13, pp. 367-383, John Wiley & Sons N.Y.

Alayash and Cashon, "Hemoglobin and free radicals: implications for the development of a safe blood substitute," *Molec. Med. Today*, 1995, 1(3):122-127.

Ashwell, "Carbohydrate Antigens: Coupling of Carbohydrates to Proteins by a Mixed Anhydride Reaction," *Meth. Enzymol.*, 1972, 28:219-222.

Avigad, "A Simple Spectrophotometric Determination of Formaldehyde and Other Aldehydes: Application to Periodate-Oxidized Glycol Systems," *Anal. Biochem.*, 1983, 134:499-504.

Baldwin et al., "Synthesis of Polymer-Bound Hemoglobin Samples," *Tetrahedron*, 1981, 37:1723-1726.

Balland et al., "Intracellular distribution of ampicillin in murine macrophages infected with *Salmonella typhimurium* and treated with ($^3$H)ampicillin-loaded nanoparticles," *J. Antimicrob. Chemother.*, 1996, 37:105-115.

Barbone et al., "Reticulocyte measurements as a bioassay for erythropoietin," *J. Pharm. Biomed. Anal.*, 1994, 12(4):515-522.

Bårström et al., "New derivatives of reducing oligosaccharides and their use in enzymatic reactions: efficient synthesis of sialyl Lewis a and sialyl dimeric Lewis x glycoconjugates," *Carbohydr. Res.*, 2000, 328:525-531.

Bauer et al., "Synthesis of w—(Aminooxy)alkanethiols," *J. Org. Chem.*, 1965, 30:949-951.

Bauer and Suresh, "S-[w-(Aminoöxy)alkyl]isothiuronium Salts, w,w'-Bis(aminoöxy)alkanes and Related Compounds," *J. Org. Chem.*, 1963, 28:1604-1608.

Bendele et al., "Short Communication: Renal Tubular Vacuolation in Animals Treated with Polyethylene-Glycol-Conjugated Proteins," *Toxicol. Sci.*, 1998, 42:152-157.

Benesch, "Bis(pyridoxal) Polyphosphates as Specific Intramolecular Cross-Linking Agents for Hemoglobin," *Meth. Enzymol.*, 1994, 231:267-274.

Bepperling et al., "HES 130/0.4, a new HES specification: tissue storage after multiple infusions in rats," *Crit. Care*, 1999, 3(suppl 1):P153.

Berger et al., "Galactosyltransferase-dependent sialylation of complex and endo-*N*-acetylglucosaminidase H-treated core *N*-glycans in vitro," *FEBS Lett.*, 1986, 203(1):64-68.

Black et al., "*N*-Bromoacetyl-glycopyranosylamines as affinity labels for a β-glucosidase and a cellulase," *Carbohydr. Res.*, 1993, 250:195-202.

Bobbitt, "Periodate Oxidation of Carbohydrates," *Carbohydr. Chem.*, 1956, 11:1-41.

Boissel et al., "Erythropoietin Structure-Function Relationships. Mutant proteins that test a model of tertiary structure," *J. Biol. Chem.*, 1993, 268(21):15983-15993.

Boturyn et al., "Synthesis of Fluorescent Probes for the Detection of Abasic Sites in DNA," *Tetrahedron*, 1997, 53(15):5485-5492.

Bowen et al., "Estimation of Effective and Total Erythropoiesis in Myelodysplasia Using Serum Transferrin Receptor and Erythropoietin Concentrations, with Automated Reticulocyte Parameters," *Leukemia*, 1994, 8(1):151-155.

Bronzino, *The Biomedical Engineering Handbook*, CRC Press, USA, Salem, 1995, (TOC only).

Bunn & Jandl, "The Real Handling of Hemoglobin. II. Catabolism," *J. Exp. Med.*, 1967, 129:925-934.

Burgess et al., "Stimulation by Human Placental Conditioned Medium of Hemopoietic Colony Formation by Human Marrow Cells," *Blood*, 1977, 49(4):573-583.

Bystrický et al., "Determination of the cross-linking effect of adipic acid dihydrazide on glycoconjugate preparation," *Glycoconj. J.*, 1999, 16:691-695.

Cabacungan et al., "Amine Boranes as Alternative Reducing Agents for Reductive Alkylation of Proteins," *Anal. Biochem.*, 1982, 124:272-278.

Carlsson et al., "Protein Thiolation and Reversible Protein-Protein Conjugation," *Biochem J.*, 1978, 173:723-737.

Cerami, "Beyond Erythropoiesis: Novel Applications for Recombinant Human Erythropoietin," *Semin. Hematol.*, 2001, 38:(3 Suppl 7):33-39.

Cerny et al., "A Hydroxyethyl Starch-Hemoglobin Polymer as a Blood Substitute," *Clinical Hemorheology*, 1982, 2(4):355-365.

Chamow et al., "Conjugation of Soluble CD4 without Loss of Biological Activity via a Novel Carbohydrate-directed Cross-linking Reagent," *J. Biol. Chem.*, 1992, 267(22):15916-15922.

Chang, "Blood Substitutes Based on Modified Hemoglobin Prepared by Encapsulation or Crosslinking: An Overview," *Biomat., Art. Cells & Immob. Biotech.*, 1992, 20:159-179.

Chagnon et al., "Murine renal cell carcinoma: evaluation of a dendritic-cell tumour vaccine," *BJU Int.*, 2001, 88:418-424.

Chaplin, "Monosaccharides," *Carbohydrate analysis: a practical approach*, 1996, Chaplin and Kennedy (eds.), Chapter 1, "Oligosaccharides," pp. 37-54.

Chaplin, "A Rapid Sensitive Method for the Analysis of Carbohydrate Components in Glycoproteins Using Gas-Liquid Chromatography," *Anal. Biochem.*, 1982, 123:336-341.

Chapman et al., "Therapeutic antibody fragments with prolonged in vivo half-lives," *Nature Biotech.*, 1999, 17:780-783.

Chow et al., "In vitro Induction of apoptosis of neoplastic cells in low-grade non-Hodgkin's lymphomas using combinations of established cytotoxic drugs with bendamustine," *Haematologica*, 2001, 86:485-493.

Chu et al., "Further Studies on the Immunogenicity of *Haemophilus influenzae* Type b and Pneumococcal Type 6A Polysaccharide-Protein Conjugates," *Infect. Immun.*, 1983, 40:245-256.

Cumber et al., "Preparation of Antibody-Toxin Conjugates," *Meth. Enzymol.*, 1985, 112:207-225.

Delgado et al., "The Uses and Properties of PEG-Linked Proteins," *Crit. Rev. Ther. Drug Carrier Syst.*, 1992, 9(3,4):249-304.

Delorme et al., "Role of Glycosylation on the Secretion and Biological Activity of Erythropoietin," *Biochemistry*, 1992, 31(41):9871-9876.

Dittmar et al., "Human Glycoproteins and Derived Variants from Recombinant Mammalian Cell Lines," *Advances in Protein Design*, 1989, 12:145-156.

Dorner et al., "Increased Synthesis of Secreted Proteins Induces Expression of Glucose-regulated Protein in Butyrate-treated Chinese Hamster Ovary Cells," *J. Biol. Chem.*, 1989, 264(34):20602-20607.

Dowling and Russell, "Pharmacokinetics of a long-acting oxytetracycline-polyethylene glycol formulation in horses," *J. Vet. Pharmacol. Therap.*, 2000, 23:107-110.

Dreborg and Åkerblom, "Immunotherapy with Monomethoxypolyethylene Glycol Modified Allergens," *Crit. Rev. Ther. Drug Carrier Syst.*, 1990, 6(4):315-365.

Blum et al., "Improved silver staining of plant proteins, RNA and DNA in polyacrylamide gels," *Electrophoresis*, 1987, 8:93-99.

Elliott et al., "Mapping of the Active Site of Recombinant Human Erythropoietin," *Blood*, 1997, 89(2): 493-502.

European Pharmacopoeia, "Erythropoietin Concentrated Solution," 3rd Edition, 2000, Monography, pp. 655-660.

European Pharmacopoeia, "Erythropoietin Concentrated Solution," 4th Edition, 2002, Monography, pp. 1123-1128.

Fernández-Santana et al., "Conjugation of 5-azido-3-oxapentyl glycosides with thiolated proteins through the use of thiophilic derivatives," *Glycoconj. J.*, 1998, 15:549-553.

Fibi et al., "Evidence for the Location of the Receptor-Binding Site of Human Erythropoietin at the Carboxyl-Terminal Domain," *Blood*, 1991, 77(6):1203-1210.

Fibi et al., "N- and O-Glycosylation Muteins of Recombinant Human Erythropoietin Secreted From BHK-21 Cells," *Blood*, 1995, 85(5):1229-1236.

Fissekis et al., "*N*-Pantoyl-(substituted)amines, Pantothenic Acid Analogues," *J. Med. Pharm. Chem.*, 1960, 2:47-56.

Forno et al., "N- and O-linked carbohydrates and glycosylation site occupancy in recombinant human granulocyte-macrophage colony-stimulating factor secreted by a Chinese hamster ovary cell line," *Eur. J. Biochem.*, 2004, 271:907-919.

Gaertner and Offord, "Site-Specific Attachment of Functionalized Poly(ethylene glycol) to the Amino Terminus of Proteins," *Bioconjugate Chemistry*, 1996, 7(1):38-44.

Gervais et al., "NMR investigations of the role of the sugar moiety in glycosylated recombinant human granulocyte-colony-stimulating factor," *Eur. J. Biochem.*, 1997, 247:386-395.

Gillis et al., "T Cell Growth Factor: Parameters of Production and a Quantitative Microassay for Activity," *J. Immunol.*, 1978, 120(6):2027-2032.

Gonzalez Lio and Thiem, "Chemoenzymatic synthesis of spacer-linked oligosaccharides for the preparation of neoglycoproteins," *Carbohydr. Res.*, 1999, 317:180-190.

Gould et al., "The Development of Hemoglobin Solutions as Red Cell Substitutes: Hemoglobin Solutions," *Transfus. Sci.*, 1995, 16:5-17.

Grabenhorst et al., "Construction of stable BHK-21 cells coexpressing human secretory glycoproteins and human Gal(β1-4)GlcNAc-R α2,6-sialyltransferase: α2,6-Linked NeuAc is preferentially attached to the Gal(β1-4)GlcNAc(β1-2)Man(α1-3)-branch of diantennary oligosaccharides from secreted recombinant β-trace protein," *Eur. J. Biochem.*, 1995, 232:718-725.

Grabenhorst and Conradt, "The Cytoplasmic, Transmembrane, and Stem Regions of Glycosyltransferases Specify Their in vivo Functional Sublocalization and Stability in the Golgi," *J. Biol. Chem.*, 1999, 274(51):36107-36116.

Grabenhorst et al., "Biosynthesis and secretion of human interleukin 2 glycoprotein variants from baculovirus-infected Sf21 cells. Characterization of polypeptides and posttranslational modifications," *Eur. J. Biochem.*, 1993, 215:189-197.

Grabenhorst et al., "In Vivo Specificity of Human α1,3/4-Fucosyltransferases III-VII in the Biosynthesis of Lewis$^x$ and Sialyl Lewis$^x$ Motifs on Complex-type N-Glycans. Coexpression studies from BHK-21 cells together with human β-trace protein," *J. Biol. Chem.*, 1998, 273(47):30985-30994.

Grabenhorst et al., "Genetic engineering of recombinant glycoproteins and the glycosylation pathway in mammalian host cells," *Glycoconj J.*, 1999, 16(2):81-97.

Gray, "The Direct Coupling of Oligosaccharides to Proteins and Derivatized Gels," *Arch. Biochem. Biophys.*, 1974, 163:426-428 (Fig. 2.1a).

Greenfield et al., "Evaluation in Vitro of Adriamycin Immunoconjugates Synthesized Using an Acid-sensitive Hydrazone Linker," *Cancer Research*, 1990, 50:6600-6607.

Grimmecke and Brade, "Studies on the reductive amination of 3-deoxy-D-*manno*-octulosonic acid (Kdo)," *Glycoconj. J.*, 1998, 15:555-562.

Habeeb, "Determination of Free Amino Groups in Proteins by Trinitrobenzenesulfonic Acid," *Anal. Biochem.*, 1966, 14:328-336.

Hai et al., "Diaspirin Crosslinked Hemoglobin (DCLHb™) Polymerization," *Art. Cells. Blood Subs., and Immob. Biotech.*, 1994, 22(3):923-931.

Hallaway et al., "Modulation of Deferoxamine Toxicity and Clearance by Covalent Attachment to Biocompatible Polymers," *Proc. Natl. Acad. Sci. USA*, 1989, 86:10108-10112.

Hamma and Miller et al., "4-(2-Aminooxyethoxy)-2-(ethylureido)quinoline-Oligonucleotide Conjugates: Synthesis, Binding Interactions, and Derivatization with Peptides," *Bioconj. Chem.*, 2003, 14:320-330.

Hartman and Wold, "Cross-Linking of Bovine Pancreative Ribonuclease A with Dimethyl Adipimidate," *Biochemistry*, 1967, 6(8):2439-2448.

Hashimoto et al., "Chemical Modification of the Reducing Chain End in Dextrans and Trimethylsilylation of Its Hydroxyl Groups," *J. Polymer Science: Part A: Polymer Chemistry*, 1991, 29:1271-1279.

Hattori et al., "Reduced Immunogenicity of β-Lactoglobulin by Conjugation with Carboxymethyl Dextran," *Bioconjug. Chem.*, 2000, 11:84-93.

Herman et al., "Characterization, Formulation, and Stability of Neupogen® (Filgrastim), a Recombinant Human Granulocyte-Colony Stimulating Factor," *Formulation, Characterization, and Stability of Protein Drugs*, Pearlman and Wang (eds.), Plenum Press, Chapter 7, 1996, pp. 303-328.

Hermanson, *Bioconjugate Techniques*, 1996 (TOC only).

Hermentin et al., "A Strategy for the Mapping of N-Glycans by High-pH Anion-Exchange Chromatography with Pulsed Amperometric Detection," *Anal. Biochem.*, 1992, 203(2):281-289.

Higuchi et al., "Role of Sugar Chains in the Expression of the Biological Activity of Human Erythropoietin," *J. Biol. Chem.*, 1992, 267(11):7703-7709.

Sharaf et al., "Studies on Aroyl- and Aryl-Hydrazide Derivatives from D-*glycero*-D-*gulo*-Heptono-1,4-Lactone," *Carbohydrate Res.*, 1981, 91:39-48.

Inoue et al., "An Improved Method for the Purification of Human Erythropoietin with High in Vivo Activity from the Urine of Anemic Patients," *Biol. Pharm. Bull.*, 1994, 17(2):180-184.

Iwamoto et al., "Polysaccharide-Coated Oil Droplets in Oil-in-Water Emulsions as Targetable Carriers for Lipophilic Drugs," *J. Pharm. Sci.*, 1991, 80(3):219-224.

Jia et al., "S-nitrosohaemoglobin: a dynamic activity of blood involved in vascular control," *Nature*, 1996, 380:221-226.

Jones et al., "A convenient synthesis of N-(*tert*-butyloxycarbonyl)aminooxy ethers," *Tetrahedron Letters*, 2000, 41(10):1531-1533.

Jones et al., "Multivalent Poly(ethylene glycol)-Containing Conjugates for In Vivo Antibody Suppression," *Bioconj. Chem.*, 2003, 14(6):1067-1076.

Kallin, "Coupling of Oligosaccharides to Proteins Using *p*-Trifluoroacetamidoaniline," *Meth. Enzymol.*, 1994, 242:119-123.

Keaney, Jr. et al., "No Forms an Adduct with Serum Albumin that Has Endothelium-derived Relaxing Factor-like Properties," *J. Clin. Invest.*, 1993, 91:1582-1589.

Keipert et al., "Functional properties of a new crosslinked hemoglobin designed for use as a red cell substitute," *Transfusion*, 1989, 29:768-773.

Kitamura et al., "Establishment and Characterization of a Unique Human Cell Line That Proliferates Dependently on GM-CSF, IL-3, or Erythropoietin," *J. Cell. Phys.*, 1989, 140:323-334.

Kitamura et al., "Chemical Engineering of the Monoclonal Antibody A7 by Polyethylene Glycol for Targeting Cancer Chemotherapy," *Cancer Res.*, 1991, 51:4310-4315.

Kleine-Tebbe et al., "Allergen Immunotherapy—A Position Paper of the German Society for Allergology and Clinical Immunology," *Pneumologie*, 2001, 55:438-444 (w/English summary).

Klemm et al., "Esterification of Cellulose," *Comprehensive Cellulose Chemistry*, 1998, vol. 2, Wiley-VCH, Weinheim, New York, especially chapter 4.4, pp. 99-207.

Kobayashi et al., "Reduced Immunogenicity of β-Lactoglobulin by Conjugation with Carboxymethyl Dextra Differing in Molecular Weight," *J. Agric. Food Chem.*, 2001, 49(2):823-831.

Kojima et al., "Mitomycin C-dextran conjugate: a novel high molecular weight pro-drug of mitomycin C," *J. Pharm. Pharmacol.*, 1980, 32:30-34.

Komatsu et al., "Cloning of granulocyte colony-stimulating factor cDNA from human macrophages and its expression in *Escherichia coli*," *Jpn. J. Cancer Res.*, 1987, 78(11):1179-1181.

Krantz, "Erythropoietin," *Blood*, 1991, 77(3):419-434.

Krystal, "Physical and Biological Characterization of Erythroblast Enhancing Factor (EEF), a Late Acting Erythropoietic Stimulator in Serum Distinct from Erythropoietin," *Exp. Hematol.*, 1983, 11(1):18-31.

Krystal, "A Simple Microassay for Erythropoietin Based on $^3$H-Thymidine Incorporation into Spleen Cells from Phenylhydrazine Treated Mice," *Exp. Hematol.*, 1983, 11(7):649-660.

Krystal et al., "Purification of Human Erythropoietin to Homogeneity by a Rapid Five-Step Procedure," *Blood*, 1986, 67(1):71-79.

Kuberan et al., "Preparation and isolation of neoglycoconjugates using biotin-streptavidin complexes," *Glycoconj. J.*, 1999, 16:271-281.

Kurtz and Eckardt, "Assays for Erythropoietin," *Nephron.*, 1989, 51(suppl 1):11-14 (w/English summary).

Larionova et al., "Conjugation of the Bowman-Birk Soybean Proteinase Inhibitor with Hydroxyethylstarch," *Appl. Biochem. Biotech.*, 1997, 62:175-182.

Lee (ed.), "Synthesis of Peptides and Proteins," *Peptide and Protein Drug Delivery*, 1991, p. 65.

Lee and Lee, "Neoglycoproteins," *Glycoproteins II*, 1997, Chapter 17, Elsevier Science B.V., pp. 301-620.

Leenders et al., "β-Glucuronyl Carbamate Based Pro-moieties Designed for Prodrugs in ADEPT," *Tetrahedron Letters*, 1995, 36(10):1701-1704.

Lees et al., "Actication of soluble polysaccharides with 1-cyano-4-dimethylaminopyridinium tetrafluoroborate for use in protein-polysaccharide conjugate vaccines and immunological reagents," *Vaccine*, 1996, 14(3):190-198.

Lesnefsky et al., "High-Dose Iron-Chelator Therapy During Reperfusion with Deferoxamine-Hydroxyethyl Starch Conjugate Fails to Reduce Canine Infarct Size," *J. Cardiovasc. Pharmacol.*, 1990, 16(4):523-528.

Lin et al., "Cloning and expression of the human erythropoietin gene," *Proc. Natl. Acad. Sci. USA*, 1985, 82:7580-7584.

Lindsey at al., "Porphyrin Building Blocks for Modular Construction of Bioorganic Model Systems," *Tetrahedron*, 1994, 50(30):8941-8968, especially p. 8956.

Lomant and Fairbanks, "Chemical Probes of Extended Biological Structures: Synthesis and Properties of the Cleavable Protein Cross-linking Reagent [$^{35}$S]Dithiobis(succinimidyl propionate)," *J. Mol. Biol.*, 1976, 104:243-261.

Lönngren and Goldstein, "Coupling of Aldobionic Acids to Proteins Using Water-Soluble Carbodiimide," *Meth. Enzymol.*, 1994, 242:116-118.

Manger et al., "1-*N*-Glycyl β-Oligosaccharide Derivatives as Stable Intermediates for the Formation of Glycoconjugate Probes," *Biochemistry*, 1992, 31:10724-10732.

Manger et al., "Synthesis of 1-*N*-Glycyl β-Oligosaccharide Derivatives. Reactivity of *Lens culinaris* Lectin with a Fluorescent Labeled Streptavidin Pseudoglycoprotein and Immobilized Neoglycolipid," *Biochemistry*, 1992, 31:10733-10740.

Maout et al., "Hydroxyethylstarch Conjugated to Human Hemoglobin for use in Blood Transfusion: Comparison with Dextran Conjugates," *Carbohydrates and Carbohygrate Polymers—Analysis, Biotechnology, Modification, Antiviral and Other Applications*, 1993, Chapter 12, pp. 132-140.

McMahon et al., "Pharmacokinetics and Effects of Recombinant Human Erythropoietin After Intravenous and Subcutaneous Injections in Healthy Volunteers," *Blood*, 1990, 76(9):1718-1722.

Meinjohanns et al., "Novel sequential solid-phase synthesis of N-linked glycopeptides from natural sources," *J. Chem. Soc., Perkin Trans. 1*, 1998, 1:549-560.

Mikola and Hänninen, "Introduction of Aliphatic Amino and Hydroxy Groups to Keto Steroids Using O-Substituted Hydroxylamines," *Bioconj. Chem.*, 1992, 3(2):182-186.

Minnema et al., "Recombinant human antithrombin III improves survival and attenuates inflammatory responses in baboons lethally challenged with *Escherichia coli*," *Blood*, 2000, 95(4):1117-1123.

Miyake et al., "Purification of Human Erythropoietin," *J. Biol. Chem.*, 1977, 252(15):5558-5564.

Montreuil et al., "Hexuronic acids," *Carbohydrate analysis: a practical approach*, 1996, Chaplin and Kennedy (eds.), Chapter 5, pp. 175-204.

Mosbech et al., "Hyposensitization in asthmatics with mPEG-modified and unmodified house dust mite extract," *Allergy*, 1990, 45(2):130-141.

Mosmann, "Rapid Colorimetric Assay for Cellular Growth and Survival: Application to Proliferation and Cytotoxicity Assays," *J. Immunol. Meth.*, 1983, 65:55-63.

Mueller et al., "Recombinant Glycoprotein Product Quality in Proliferation-Controlled BHK-21 Cells," *Biotechnol. Bioeng.*, 1999, 65(5):529-536.

Davis and Flitsch, "A Novel Method for the Specific Glycosylation of Proteins," *Tetrahedron Lett.*, 1991, 32(46):6793-6796.

Nagata et al., "The chromosomal gene structure and two mRNAs for human granulocyte colony-stimulating factor," *EMBO J.*, 1986, 5(3):575-581.

Nagata et al., "Molecular cloning and expression of cDNA for human granulocyte colony-stimulating factor," *Nature*, 1986, 319:415-418.

Nakane et al., "The Accumulation Mechanism of Cationic Mitomycin C-dextran Conjugates in the Liver: In-vivo Cellular Localization and In-vitro Interaction with Hepatocytes," *J. Pharm. Pharmacol.*, 1988, 40:1-6.

Nedospasov and Khomutov, "Synthesis and some properties of aminooxyalkylcelluloses," *Bulletin of the Academy of Sciences of the USSR*, 1976, Division of Chemical Science, Consultants Bureau, New York, 25:1105-1110.

Nimtz et al., "Structural characterization of the oligosaccharide chains of native and crystallized boar seminal plasma spermadhesin PSP-I and PSP-II glycoforms," *Eur. J. Biochem.*, 1999, 265:703-718.

Nimtz et al., "Structures of sialylated oligosaccharides of human erythropoietin expressed in recombinant BHK-21 cells," *Eur. J. Biochem.*, 1993, 213:39-56.

Nimtz et al., "Carbohydrate structures of a human tissue plasminogen activator varient expressed in recombinant Chinese hamster ovary cells," *FEBS Lett.*, 1990, 271:14-18.

Nohynek et al., "Comparison of the potency of glycosylated and nonglycosylated recombinant human granulocyte colony-stimulating factors in neutropenic and nonneutropenic CD rats," *Cancer Chemother Pharmacol.*, 1997, 39:259-266.

Nomura et al., "Pharmacokinetic characteristics and therapeutic effects of mitomycin C-dextran conjugates after intratumoural injection," *J. Controlled Release*, 1998, 52:239-252.

O'Shannessy and Wilchek, "Immobilization of Glycoconjugates by Their Oligosaccharides: Use of Hydrazido-Derivatized Matrices," *Analytical Biochemistry*, 1990, 191:1.

Pawlowski et al., "A new method of non-cross-linking conjugates of polysaccharides to protein via thioether bonds for the preparation of saccharide-protein conjugate vaccines," *Vaccine*, 1999, 17:1474-1483.

Pazur, "Neutral polysaccharides," *Carbohydrate analysis: a practical approach*, 1996, Chaplin and Kennedy (eds.), Chapter 3, pp. 55-96.

Pedley et al., "The potential for enhanced tumour localization by poly)ethylene glycol) modification of anti-CEA antibody," *Br. J. Cancer*, 1994, 70:1126-1130.

Peeters et al., "Comparison of four bifunctional reagents for coupling peptides to proteins and the effect of the three moieties on the immunogenicity of the conjugates," *J. Immunol. Meth.*, 1989, 120:133-143.

Peron et al., "Hydroxyethyl starch-induced renal insufficiency after plasma exchange in a patient with polymyositis and liver cirrhosis," *Clin. Nephrol.*, 2001, 55(5):408-411.

*Pharma Business*, Jul./Aug. 2000, pp. 45-60.

Quelle et al., "High-Level Expression and Purification of a Recombinant Human Erythropoietin Produced Using a Baculovirus Vector," *Blood*, 1989, 74(2):652-657.

Rabiner et al., "Evaluation of a stroma-free hemoglobin solution for use as a plasma expander," *J. Exp. Med.*, 1967, 126:1127-1142.

Ragupathi et al., "A novel and efficient method for synthetic carbohydrate conjugate vaccine preparation: synthesis of sialyl Tn-KLH conjugate using a 4-(4-*N*-maleimidomethyl) cyclohexane-1-carboxyl hydrazide (MMCCH) linker arm," *Glycoconj. J.*, 1998, 15:217-221.

Ramos et al., "Enzymatic Synthesis of Neoglycopeptide Building Blocks," *Angew. Chem. Int. Ed.*, 2000, 39(2):396-398.

Relihan et al., "Clearance Rate and Effect on Renal Function of Stroma-Free Hemoglobin Following Renal Ischemia," *Ann. Surg.*, 1972, 176(6):700-704.

Richter and de Belder, "Antibodies against Hydroxyethylstarch Produced in Rabbits by Immunization with a Protein-Hydroxyethylstarch Conjugate," *Int. Arch. Allergy Appl. Immun.*, 1976, 52:307-314.

Rogers et al., "Effects of polymerization on the oxygen carrying and redox properties of diaspirin cross-linked hemoglobin," *Biochim. Biophys. Acta*, 1995, 1248:135-142.

Rohrling et al., "Synthesis and testing of a novel fluorescene label for carbonyls in carbohydrates and cellulosics," *Synlett*, 2001, 5:682-684.

Rose, "Facile Synthesis of Homogeneous Artificial Proteins," *J. Am. Chem. Soc.*, 1994, 116:30-33.

Rudolph et al., "Circulation persistence and biodistribution of lyophilized liposome-encapsulated hemoglobin: An oxygen-carrying resuscitative fluid," *Crit. Care Med.*, 1994, 22:142-150.

Rudolph, "The Freeze-Dried Preservation of Liposome Encapsulated Hemoglobin: A Potential Blood Substitute," *Cryobiology*, 1988, 25:277-284.

Rush et al., "Microheterogeneity of Erythropoietin Carbohydrate Structure," *Anal. Chem.*, 1995, 67(8):1442-1452.

Ruttmann et al., "In vivo investigation into the effects of haemodilution with hydroxyethylstarch (200/0.5) and normal saline on coagulation," *Br. J. Anaesthesia*, 1998, 80(5):612-616.

Sadamoto et al., "Control of Bacteria Adhesion by Cell-Wall Engineering," *J. Am. Chem. Soc.*, 2004, 126:3755-3761.

Sadrzadeh et al., "The Long-Acting Parenteral Iron Chelator, Hydroxyethyl Starch-Deferoxamine, Fails to Protect Against Alcohol-Induced Liver Injury in Rats," *J. Pharmacol. Exp. Ther.*, 1997, 280(2):1038-1042.

Sakai et al., "Synthesis and Physicochemical Characterization of a Series of Hemoglobin-Based Oxygen Carries: Objective Comparison between Cellular and Acellular Types," *Bioconj. Chem.*, 2000, 11:56-64.

Sato et al., "Disposition of a Polymeric Prodrug of Mitomycin C, Mitomycin C-Dextran Conjugate, in the Perfused Rat Liver," *J. Pharm. Sci.*, 1989, 78:11-16.

Sawaikar et al., "Products active on mosquitoes. Part VII, Synthesis and biological activity of longifolene derivatives," *Indian Journal of Chemistry*, 1995, 34B:832-835.

Scaglione et al., "A New Model Examining Intracellular and Extracellular Activity of Amoxicillin, Azithromycin, and Clarithromycin in Infected Cells," *Chemotherapie*, 1993, 39:416-423.

Schäfer et al., "Two-year double-blind trial of a monomethoxy polyethylene glycol (mPEG) modified grass pollen extract at different dose levels," *Ann. Allergy*, 1992, 68(4):334-339.

Schlenke et al., "Construction and characterization of stably transfected BHK-21 cells with human-type sialylation characteristic," *Cytotechnology*, 1999, 30:17-25.

Schottelius et al., "Improvement of Pharmacokinetics of Radioiodinated $Tyr^3$-Octreotide by Conjugation with Carbohydrates," *Bioconjugate Chem.*, 2002, 13:1021-1030.

Shafer et al., "Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides," *Vaccine*, 2000, 18:1273-1281.

Shah et al., "Characterization of Colony-stimulating Activity Produced by Human Monocytes and Phytohemagglutinin-stimulated Lymphocytes," 1977, *Blood*, 50(5):811-821.

Shirafuji et al., "A new bioassay for human granulocyte colony-stimulating factor (hG-CSF) using murine myeloblastic NFS-60 cells as targets and estimation of its levels in sera from normal healthy persons and patients with infectious and hematological disorders," *Exp. Hematol.*, 1989, 17:116-119.

Simmons et al., "Potent inhibition of HIV-1 infectivity in microphages and lymphocytes by a novel CCR5 antagonist," *Science*, 1997, 276:276-279.

Snyder et al., "HbXL99α A hemoglobin derivative that is cross-linked between the α subunits is useful as a blood substitute," *Prob. Natl. Acad. Sci. USA*, 1987, 84:7280-7284.

Shu, "Somogyi Micro Copper Method," *Method in Carbohydride Chemistry*, 1962, 1:383-388.

Song et al., "Toxicity and Antitumor Activity of the Conjugate of Mitomycin C with Carboxymethyl-chitin," *Arch. Pract. Pharm.*, 1993, 53(3):141-147.

Souza et al., "Recombinant human granulocyte colony-stimulating factor: effects on normal and leukemic myeloid cells," *Science*, 1986, 232:61-65.

Soyez et al., "Biological evaluation of mitomycin C bound to a biodegradable polymeric carrier," *J. Controlled Release*, 1997, 47:71-80.

Spivak and Hogans, "The In Vivo Metabolism of Recombinant Human Erythropoietin in the Rat," *Blood*, 1989, 73:90-99.

Staros, "N-Hydroxysulfosuccinimide Active Esters: Bis(N-hydroxysulfosuccinimide) Esters of Two Dicarboxylic Acids Are Hydrophilic, Membrane-Impermeant, Protein Cross-Linkers," *Biochemistry*, 1982, 21:3950-3955.

Sunamoto and Iwamoto, "Protein-Coated and Polysaccharide-Coated Liposomes as Drug Carriers," *CRC Critical Review in Therapeutic Drug Carrier Systems*, 1986, 2:117-136.

Sytkowski et al., "Human erythropoietin dimers with markedly enhanced in vivo activity," *Proc. Natl. Acad. Sci. USA*, 1998, 95(3):1184-1188.

Sytkowski et al., "An Erythropoietin Fusion Protein Comprised of Identical Repeating Domains Exhibits Enhanced Biological Properties," *J. Biol. Chem.*, 1999, 274(35):24773-24778.

Takeuchi et al., "Relationship between sugar chain structure and biological activity of recombinant human erythropoietin produced in Chinese hamster ovary cells," *Proc. Natl. Acad. Sci. USA*, 1989, 86:7819-7822.

Takeuchi and Kobata, "Structures and functional roles of the sugar chains of human erythropoietins," *Glycobiology*, 1991, 1(4):337-346.

Tam et al., "Soluble Dextran-Hemoglobin Complex as a Potential Blood Substitute," *Proc. Natl. Acad. Sci. USA*, 1976, 73(6):2128-2131.

Tanaka et al., "Pharmacokinetics of recombinant human granulocyte colony-stimulating factor conjugated to polyethylene glycol in rats," *Cancer Research*, 1991, 51:3710-3714.

Thomas et al., "Measuring blood volume with fluorescent-labeled hydroxyethyl starch," *Crit. Care Med.*, 2000, 28(3):627-631.

Thomas, "Carbohydrate Binding Sites," *Meth. Enzymol.*, 1977, 46:362-368.

Thorpe et al., "Blockade of the galactose-binding sites of ricin by its linkage to antibody," *Eur. J. Biochem.*, 1984, 140:63-71.

Toyama et al., "Surface design of SPR-based immunosensor for the effective binding of antigen or antibody in the evanescent field using mixed polymer matrix," *Sensors and Actuators B*, 1998, 52:65-71.

De Velasco et al., "Synthetic Peptides Representing T-Cell Epitopes Act as Carriers in Pneumococcal Polysaccharide Conjugate Vaccines," *Infect. Immun.*, 1995, 63(3):961-968.

Van Pattern et al., "Oxidation of Methionine Residues in Antithrombin," *J. Biol. Chem.*, 1999, 274(15):10268-10276.

Veronese et al., "Surface Modification of Proteins. Activation of Monomethoxy-Polyethylene Glycols by Phenylchloroformates and Modification of Ribonuclease and Superoxide Dismutase," *Appl. Biochem. Biotech.*, 1985, 11:141-152.

Vilaseca et al., "Protein conjugates of defined structure: Synthesis and use of a new carrier molecule," *Bioconjugate Chemistry*, 1993, 4(6):515-520.

Webb II and Kaneko, "Synthesis of 1-(Aminooxy)-4-[(3-nitro-2-pyridyl)dithio]butane and 1-(Aminooxy)-4-[(3-nitro-2-pyridyl)dithio]but-2-ene, Novel Heterobifunctional Cross-Linking Reagents," *Bioconjugate Chem.*, 1990, 1:96-99.

Weidler et al., "Pharmakokinetische Merkmale als Kriterien für den klinischen Einsatz von Hydroxyethylstärke," *Arzneim.-Forsch./Drug Res.*, 1991, 41:494-498 (w/English summary).

White and Kennedy, "Oligosaccharides," *Carbohydrate analysis: a practical approach*, 1996, Chaplin and Kennedy (eds.), Chapter 2, pp. 1-36.

Whitesides et al., "Rates of Thiol-Disulfide Interchange Reactions between Mono- and Dithiols and Ellman's Reagent," *J. Org. Chem.*, 1977, 42(2):332-338.

Wong et al., "Analysis of carbohydrate-protein interactions with synthetic N-linked neoglycoconjugate probes," *Biochem. J.*, 1993, 296:817-825.

Wong et al., "Synthetic glycosylation of proteins using N-(β-saccharide) iodoacetamides: applications in site-specific glycosylation and solid-phase enzymic oligosaccharide synthesis," *Biochem. J.*, 1994, 300:843-850.

Wong, *Chemistry of protein conjugation and cross-linking*, 1993, CRCS, Inc. (TOC only).

Xue and Wong; "Preparation of Conjugated Hemoglobins," *Meth. Enzymol.*, 1994, 231:308-322.

Yalpani et al., "Selective Chemical Modifications of Dextran," *J. Polymer Science: Polymer Chemistry Edition*, 1985, 23:1395-1405.

Yamaguchi et al., "Effects of site-directed removal of N-glycosylation sites in human erythropoietin on its production and biological properties," *J. Biol. Chem.*, 1991, 266(30):20434-20439.

Yoshida, "Glycamine Formation via Reductive Amination of Oligosaccharides with Benzylamine," *Meth. Enzymol.*, 1994, 247:55-64.

Zalipsky, "Functionalized Poly(ethylene glycol) for Preparation of Biologically Relevant Conjugates," *Bioconjugate Chem.*, 1995, 6:150-165.

Zara et al., "A Carbohygrate-Directed Heterobifunctional Cross-Linking Reagent for the Synthesis of Immunoconjugates," *Anal. Biochem.*, 1991, 194:156-162.

Zettlmeissl et al., "Characterization of Recombinant Human Antithrombin III Synthesized in Chinese Hamster Ovary Cells," *J. Biol. Chem.*, 1989, 264 (35):21153-21159.

Zhou et al., "Application of capillary electrophoresis, liquid chromatography, electrospray-mass spectrometry and matrix-assisted laserdesorption/ionization—time of flight—mass spectrometry to the characterization of recombinant human erythropoietin," *Electrophoresis*, 1998, 19(13):2348-2355.

Zou et al., "Allylmalonamide as a bivalent linker: Synthesis of biantennary $Gm_3$-saccharide-Keyhole limpet hemocyanin glycoconjugate and the immune response in mice," *Glycoconj. J.*, 1999, 16:507-515.

Zucali and Sulkowski, "Purification of human urinary erythropoietin on controlled-pore glass and silicic acid," *Exp. Hematol.*, 1985, 13(3):833-837.

Cera C. et al., "Water-Soluble Polysaccharide-Anthracycline Conjugates: Biological Activity, Anti-Cancer Drug Design," vol. 7, No. 2, Apr. 1992 (Apr. 1992), pp. 143-151, XP000791063, ISSN: 0266:9536.

* cited by examiner

| Drug | H | G | F | E | D | C | B | A |
|---|---|---|---|---|---|---|---|---|
| content [µg/ml] | 10 | 5 | 2,5 | 1,25 | 0.625 | 0,31 | 0,156 | 0,078 |

Positive effect
Negative effect

Amphotericin B, not filtered, in PBS (1%DMSO initial content)       MIC 0,078µg/ml
Amphotericin B, not filtered, in PBS (1%DMSO initial content)
Mlt-AmpB, not filtered, in PBS       MIC 0,31µg/ml
Mlt-AmpB, not filtered, in PBS
Mlt-AmpB, filtered, in PBS       MIC 0,31µg/ml
Mlt-AmpB, filtered, in PBS

PHARMACEUTICALLY ACTIVE OLIGOSACCHARIDE CONJUGATES

CROSS-REFERENCE TO RELATED APPLICATIONS

This application is a National Stage application under 35 U.S.C. § 371 and claims benefit under 35 U.S.C. § 119(a) of International Application No. PCT/EP03/011129 having an International Filing Date of Oct. 8, 2003, which claims the benefit of priority of European Patent Application No. 03008177.2, filed Apr. 8, 2003, and German Patent Application No. 20215415.7, filed Oct. 8, 2002.

The present invention relates to pharmaceutically active oligosaccharide conjugates having the formula $(X-Y_m)_n-$S, wherein component X is a pharmaceutically active compound, Y is a bifunctional linker, and S is an oligosaccharide, consisting of 1 to 20 saccharide units, n is equal or less than the number of the saccharide units in the oligosaccharide S, and m is, independent of n, 0 or 1.

In addition, the present invention is directed to a process of preparing compounds of the present invention, comprising the step of coupling components X and S directly or indirectly by means of a bifunctional linker group.

Furthermore, the present invention relates to the use of said pharmaceutically active oligosaccharide conjugates as a medicament as well as to pharmaceutical compositions, freeze-dried pharmaceutical compositions, and a kit, all of which comprise at least one of said pharmaceutically active oligosaccharide conjugates.

FIELD OF THE INVENTION

Many low molecular weight pharmaceutically active molecules are drastically limited in their medical application or even not used at all because of an insufficient solubility in aqueous solutions. Besides other undesirable effects this often results in a substantial decrease in bioavailability. In spite of this drawback, some drugs are administered because of a lack of suitable alternatives. In those instances the galenic formulation may, e.g., be an oily bolus or an emulsion, both of which often result in a painful deposition thereof at the injection site.

As an even more severe side effect, a lack in solubility can lead to accumulation phenomena of the drug in one or more body compartments or organs (liver, kidney, etc.) which is generally accompanied by toxic side effects. In addition, low solubility frequently implicates a very narrow therapeutic range, resulting in a low value of the therapeutic index.

There have been a number of more or less successful strategies to overcome the drawbacks of insolubility such as, e.g., drug entrapment in soluble or insoluble matrices, liposomes targeted administration, and nanoparticles. An elegant way to solve this problem is by coupling the insoluble medical substance to a large biocompatible hydrophilic polymer, such as polyethylene glycol (PEG), dextran, starch or other water-soluble polymers.

Presently, the most widely used polymer in this respect is PEG because dextran conjugates often elicit allergic reactions in clinical application. However, PEG-conjugates have been observed to sometimes lead to side effects such as, e.g., itching, hypersensibility reactions and pancreatitis.

Hydroxyethyl starch (HES) has a more promising biocompatibility profile, and has a well-known, predictable pharmacokinetic behaviour. Moreover, it is much more versatile in terms of its molecular weight availability (e.g. it may be produced from 10 kD to >500 kD) than synthetic polymers like PEG. It has also been accepted as being safer than PEG due to its well investigated degradation pathway.

Nevertheless, hydroxyethyl starch shares a common disadvantage with all other presently available polymers: its polydispersity. The polymer conjugates are always a mixture of molecules having molecular weights distributed around an average value. This lack of homogeneity results in a low level of chemical and biochemical characterization. Moreover, the polymer component may prevent the pharmaceutically active component to reach its site of action (receptor, enzyme, etc.). In these cases the drug to be active requires its delivery in the original unconjugated form, and thus cleavage of the polymer by metabolic reactions is required for its pharmaceutical efficacy.

In summary, there is still a need for stable and water soluble derivatives of pharmaceutically active compounds having an improved pharmacokinetic profile and biocompatibility in comparison to the pharmaceutically active components of the conjugates alone. Improved conjugates can be capable of hydrolytic activation under physiological conditions. Specifically, there is a need for stable and water soluble conjugates as prodrugs that can be readily metabolized to release the pharmaceutically active component in vivo. In addition, there is a need for stable and water soluble derivatives of pharmaceutically active compounds having an improved pharmacokinetic profil that are pharmaceutically active as conjugates and/or released slowly from the conjugate as to provide a delayed release form and a steric protection from metabolic enzymes.

In one aspect the present invention provides a compound having the formula:

$$(X-Y_m)_n-S,$$

wherein
X is a pharmaceutically active compound,
Y is a bifunctional linker,
S is an oligosaccharide, consisting of 1 to 20 saccharide units,
n is equal or less than the number of the saccharide units in the oligosaccharide S, and
m is, independently of n, 0 or 1.

Preferably, n is 1 to 8, more preferably 1 to 3, and most preferably 1.

In a preferred embodiment m is 0 and X and S are linked to each other by an amide, imine, secondary or tertiary amine, ether, ester, carbonate, carbamate, urea or thioester bond.

More preferably, components X and S are linked to each other by a bond
(i) involving an oxygen, nitrogen, or sulfur of component X and a carbon derivative of component S, or
(ii) involving a oxygen, nitrogen, or sulfur of a saccharide of component S and a carbon derivative of component X.

The term carbon derivative as used herein relates to those carbon derivatives that are comprised in an amide, imine, secondary or tertiary amine, ether, ester, carbonate, carbamate, urea or thioester bond.

In an alternative preferred embodiment, the present invention relates to compounds of the invention, wherein m is 1 and X and S are linked by means of a pharmaceutically acceptable linking group Y, said linking group Y preferably being linked to X and S by an amide, imine, secondary or teriary amine, ether, ester, carbonate, carbamate, urea or thioester bond and wherein the X—Y bond may be different from the Y—S bond.

The term "oligosaccharide" as used herein is defined as encompassing 1 to 20 saccharides. It is emphasized that mono-, di-, and trisaccharides are specifically included in the definition of oligosaccharides.

It was surprisingly found that many of the known insoluble drugs do not require large hydrophilic polymers to produce the desired hydrophilicity in a drug conjugate. Unexpectedly, 1 to 20 saccharide units are found to be sufficient. Conjugates according to the present invention can easily be produced with the homogeneity that is necessary for a predictable and desirable pharmacokinetic profile as well as enhanced biocompatibility.

In a preferred embodiment, S consists of 1 to 10, preferably of 2 to 7 saccharide units.

The oligosaccharide S may be linear or branched and the saccharide units within the oligosaccharide are linked to each other by α- or β(1-2), (1-4), or (1-6) bonds.

Preferably the oligosaccharide is linear, and more preferably the oligosaccharide is linear and the saccharide units within the oligosaccharide are linked by α- or β(1-4) bonds. In the most preferred embodiment, the oligosaccharide is linear and the saccharide units within the oligosaccharide are linked by α(1-4) bonds.

According to the invention it is preferred that one or more pharmaceutical component(s) X is (are) linked to a terminal saccharide unit(s) of the oligosaccharide S.

The term "terminal saccharide unit" as used herein refers to a saccharide unit that is linked to none or only one further saccharide unit in S.

In a preferred embodiment, the oligosaccharide S comprises aldose saccharide units, preferably terminal aldose saccharide units having a free reducing end. More preferably, oligosaccharide S comprises at least one saccharide unit that is linked to a compound X that is derived from an aldose monosaccharide comprising a free aldehyde group.

When using smaller oligosaccharides according to this invention yet another important advantage is the possibility to solubilize a much higher amount of the pharmaceutically active substance without yielding highly viscous solutions, that are generally observed for polymer-conjugated small molecules at high concentrations. For example, a trisaccharide (e.g., maltotrionic acid) conjugated drug in solution will achieve an almost 100 times higher concentration compared to the same drug coupled to hydroxyethyl starch with 50 kD molar mass before reaching an unacceptable viscosity value. Therefore, higher concentrations of the therapeutic component can be reached much easier with the conjugates according to this invention. As a consequence, conjugates of the invention are not only easier to handle for galenic formulations (e.g. reduced side effects such as, e.g., reduced deposition of the conjugate at the site of administration and reduced accumulation in undesired locations in a body) and clinical applications but also allow a higher therapeutic dosage in comparison to HES or PEG conjugates.

In a preferred embodiment the viscosity of conjugates according to the invention is 1-100 mPasc (Pascal x s), preferably 1-10 mPasc, more preferably 1-7 mPasc. For a review on viscosity in relation to physiology see J. D. Bronzine The biomedical engineering handbook, CRC Press, USA, Salem, 1995.

In a preferred embodiment the molar ratio of X to S is in the range of 20:1 to 1:1, preferably in the range of 15:1 to 1:1, more preferably in the range of 5:1 to 1:1. Most preferably the ratio of X to S is 1:1.

Also preferred are conjugates comprising structurally different pharmaceutically active components X. Preferably, the conjugates comprise 1 to 3 structurally different components X, more preferably 1 component X.

In a preferred embodiment, the oligosaccharide S comprises one or more of the oligosaccharide unit(s) which is (are) identical or different and each selected from the group consisting of:
  a) monosaccharides, preferably: ribose, arabinose, xylose, lyxose, allose, altrose, glucose, mannose, gulose, idose, galactose, talose, fucose;
  b) disaccharides, preferably lactose, maltose, isomaltose, cellobiose, gentiobiose, melibiose, primeverose, rutinose;
  c) disaccharide homologues, preferably maltotriose, isomaltotriose, maltotetraose, isomaltotetraose, maltopentaose, maltohexaose, maltoheptaose, lactotriose, lactotetraose;
  d) uronic acids, preferably glucuronic acid, galacturonic acid;
  e) branched oligosaccharides, preferably panose, isopanose,
  f) amino monosaccharides, preferably galactosamine, glucosamine, mannosamine, fucosamine, quinovosamine, neuraminic acid, muramic acid, lactosediamine, acosamine, bacillosamine, daunosamine, desosamine, forosamine, garosamine, kanosamine, kansosamine, mycaminose, mycosamine, perosamine, pneumosamine, purpurosamine, rhodosamine;
  g) modified saccharides, preferably abequose, amicetose, arcanose, ascarylose, boivinose, chacotriose, chalcose, cladinose, colitose, cymarose, 2-deoxyribose, 2-deoxyglucose, diginose, digitalose, digitoxose, evalose, evernitrose, hamamelose, manninotriose, melibiose, mycarose, mycinose, nigerose, noviose, oleandrose, paratose, rhodinose, rutinose, sarmentose, sedoheptulose, solatriose, sophorose, streptose, turanose, tyvelose.

In a more preferred embodiment, S comprises one or more of the saccharide unit(s) which is (are) selected from the group consisting of glucose, galactose, glucosamine, galactosamine, glucuronic acid, gluconic acid, galacturonic acid, lactose, lactotetraose, maltose, maltotriose, maltotetraose, isomaltose, isomaltotriose, isomaltotetraose, and neuraminic acid.

The pharmaceutically active compound X may be any drug compound or vitamin that lacks a desirable water solubility.

Preferably, the pharmaceutically active compound X is selected from the group consisting of:

antibiotic, anti-diabetic, anti-diuretic, anti-cholinergic, antiarrhytmic, anti-emetic, anti-epileptic, anti-histaminic, antimycotic, anti-sympathotonic, anti-thrombotic, androgenic, anti-androgenic, estrogenic, anti-estrogenic, anti-osteoporotic, anti-cancer, immuno-suppressing, vasodilatory antipyretic, analgesic, anti-inflammatory drugs, blood pressure lowering drugs, antitussiva, antidepressiva, β-blockers, and vitamins.

More preferably, the pharmaceutically active compound X is selected from the group consisting of:
  a) drugs comprising a primary amino group, preferably selected from the group consisting of:
  Albuterol, Alendronat, Amikazin, Ampicillin, Amoxicillin, Amphotericin B, Atenolol, Azathioprin, Cefaclor, Cefadroxil, Cefotaxim, Ceftazidim, Ceftriaxon, Cilastatin, Cimetidin, Ciprofloxacin, Clonidin, Colistin, Cosyntropin, Cycloserin, Daunorubicin, Doxorubicin, Desmopressin, Dihydroergotamin, Dobutamin, Dopamin, Ephedrin, Epinephrin, ε-Aminocapronsäure, Ergometrin, Esmolol, Famotidin, Flecainid, Folsäure, Flucytosin, Furosemid, Ganciclovir, Gentamicin, Glucagon, Hydrazalin, Imipenem, Isoproterenol, Ketamin, Liothyronin, Merpatricin, Metaraminol, Methyldopa, Metoclopramid, Metoprolol, Mexiletin, Mitomycin, Neomicin, Netilmicin, Nimodipin, Nystatin, Octreotid, Oxytocin, Pamidronat, Pentamidin, Phentolamin, Phenylephrin, Procainamid, Procain, Propranolol, Ritodrin, Sotalol, Teicoplanin, Terbutalin, Thiamin, Tiludronat, Tolazolin, Trimethoprim, Tromethamin, Vancomycin, Vasopressin, and Vinblastin;

b) drugs comprising a carboxylic acid group, preferably selected from the group consisting of:
Acetylcystein, Azlocillin, Aztreonam, Benzylpenicillin, Camptothecin, Cefamandol, Cefazolin, Cefepim, Cefotaxim, Cefotetan, Cefoxitin, Ceftazidim, Ceftriaxon, Cephalothin, Cilastatin, Ciprofloxacin, Clavulansäure, Dicloxacillin, ε-Aminocapronsäure, Floxacillin, Folinsäure, Furosemid, Fusidinsäure, Imipemem, Indomethacin, Ketorolac, Liothyronin, Melphalan, Methyldopa, Piperacillin, Prostacyclin, Prostaglandine, Teicoplanin, Ticarcillin and Vancomycin.

c) drugs comprising an arylic —OH group, preferably selected from the group consisting of:
Albuterol, Allopurinol, Apomorphin, Ceftriaxon, Dobutamin, Dopamin, Doxycyclin, Edrophonium, Isoproterenol, Liothyronin, Metaraminol, Methyldopa, Minocyclin, Pentazocin, Phenylephrin, Phentolamin, Propofol, Rifamycine, Ritodrin, Teicoplanin, Terbutalin, Tetracyclin and Vancomycin.

d) drugs comprising an aliphatic —OH group, preferably selected from the group consisting of Cyclosporin, Taxol and Paclitaxel.

In a preferred embodiment, the compounds of the present invention comprise a bifunctional linker, wherein the bifunctional linker selected from the group consisting of:

a) linker molecules that connect an —SH group with an amino group, preferably derived from a compound selected from the group consisting of:
AMAS (N-α(Maleimidoacetoxy)succinimide ester),
BMPS (N-β(Maleimidopropyloxy)succinimide ester),
GMBS (N-γ(Maleimidobutyryloxy)succinimide ester),
EMCS (N-ε(Maleimidocaproyloxy)succinimide ester),
MBS (m-Maleimidobenzoyl-N-hydroxysuccinimide ester),
SMCC (Succinimidyl4-(N-maleimidomethyl)-cyclohexane-1-carboxylate),
SMPB (Succinimidyl-4-(p-maleimidophenyl)butyrate),
SPDP (Succinimidyl-3-(2-pyridyldithio)propionate),
Sulfo-GMBS (N-(γ-Maleimidobutyryloxy)sulfosuccinimide ester), and
Sulfo-EMCS (N-(ε-Maleimidocaproyloxy)sulfosuccinimide ester);

b) linker molecules that connect two —SH groups, preferably derived from a compound selected from the group consisting of:
BMB (1,4-Bis-maleimidobutane),
BMDB (1,4-Bis-maleimido-2,3-dihydroxybutane),
BMH (Bis-maleimidohexane),
BMOE (Bis-maleimidoethane),
DTME (Dithio-bis-maleimidoethane),
HBVS (1,6-Hexane-bis-vinylsulfone),
BM(PEO)$_3$ (1,8-Bis-maleimidotriethyleneglycol), and
BM(PEO)$_4$ (1,11-Bis-maleimidotetraethyleneglycol);

c) linker molecules that connect two amino groups, preferably derived from a compound selected from the group consisting of:
BSOCOES (Bis-(2-(succinimidyloxycarbonyloxy)-ethyl)sulfone,
BS$^3$ (Bis-(sulfosuccinimidyl)suberateDFDNB (1,5-Difluoro-2,4-dinitrobenzene),
DMA (Dimethyladipimidate 2 HCl),
DSG (Disuccinimidyl glutarate),
DSS (Disuccinimidyl suberate), and
EGS (Ethylene glycol bis(succinimidylsuccinate), d) linker molecules that connect an —SH group and a —CHO functional groug, preferably derived from a compound selected from the group consisting of:
BMPH (N-(β-Maleimidopropionic acid)hydrazide TFA),
EMCH (N-(ε-Maleimidocaproic acid)hydrazide),
KMUH (N-(κ-Maleimidoundecanoic acid)hydrazide),
M$_2$C$_2$H (4-(N-Maleimidomethyl)cyclohexane-1-carboxylhydrazide HCl),
MPBH (4-(4-N-Maleimidophenyl)butyric acid hydrazide HCl), and
PDPH (3-(2-Pyridyidithio)propionyl hydrazide), e) linker molecules that connect an —SH group to an —OH group, preferably a compound derived from PMPI (N-(p-Maleimidophenyl)isocyanate);

f) linker molecules that connect an —SH group to a —COOH group, preferably derived from a compound selected from the group consisting of:
BMPA (N-β-Maleimidopropionic acid),
EMCA (N-ε-Maleimidocaproic acid), and
KMUA (N-κ-Maleimidoundecanoic acid);

g) linker molecules that transform an amino group into a carboxyl group, preferably derived from a compound selected from the group consisting of: MSA (Methyl-N-succinimidyladipate) and its longer and shorter chain homologues or the corresponding ethylene glycol derivatives;

h) linker molecules that transform a —COOH group into an amino group, preferably derived from a compound selected from the group consisting of: DAB (1,4-Diaminobutane) or its longer and shorter chain homologues or the corresponding ethylene glycol derivatives.

For the skilled person the preparation of the conjugates of the present invention is within his average skill and merely requires routine experimentation and optimization of standard synthesis strategies that are abundantly available in the prior art. Numerous non-degrading and selective strategies are available for linking amine, alcohol, and thiol functional groups with aldehyde, carboxylic acid or activated carboxylic acid functional groups. If component X and/or S lack the desired functional group it may be introduced by chemical derivatization of existing functional groups, the addition of suitable functional groups, or the addition of suitable functional linker molecules.

In a further aspect, the present invention relates to a process for preparing compounds according to the present invention, comprising the steps of:

a) coupling one or more pharmaceutically active compound(s) X, comprising an amino, alcohol, and/or thiol group, with one or more aldehyde group(s) of an oligosaccharide S, or b) coupling one or more pharmaceutically active compound(s) X, comprising an amino, alcohol, and/or thiol group with one or more carboxylic group(s) of an oligosaccharide S, or c) coupling one or more pharmaceutically active compound(s) X, comprising an amino, alcohol, and/or thiol group with one or more activated carboxylic group(s) of an oligosaccharide S, or d) coupling one or more pharmaceutically active compound(s) X comprising a carboxyl and/or aldehyde functional group with one or more amino, thiol, or alcohol group(s) of an oligosaccharide S.

The carboxyl group can be used as such or after a previous activation step, that yields an activated carboxylic acid group, such as, e.g. a lactone, an active ester, a symmetric anhydride, a mixed anhydride, a halogenide of a carboxylic acid or any other activated form of a carboxylic group that is suitable to produce the desired ester bond.

Preferred examples of activated carboxylic acids that may be used to practice specific embodiments of the present invention are selected from the group consisting of a lactone, an anhydride, a mixed anhydride, and a halogenide of a carboxylic acid.

Preferred examples of activated carboxylic acids are selected from the group consisting of a lactone, an anhydride, a mixed anhydride, and a halogenide of a carboxylic acid.

More preferred activated carboxylic acids are esters of p-nitrophenol; 2,4,6-trinitrophenol; p-chlorophenol; 2,4,6-trichlorophenol; pentachlorophenol; p-fluorophenol; 2,4,6-trifluorophenol; pentafluorophenol; N-hydroxybenzotriazole; N-hydroxysuccinimide;

Activated carboxylic acids can, for example, be formed by using one of the following reagents:

N-hydroxy succinimide, N-hydroxy phthalimide, thiophenol, p-nitrophenol, o,p-dinitrophenol, trichlorophenol, trifluorophenol, pentachlorophenol, pentafluorophenol, 1-hydroxy-1H-benzotriazole (HOBt), HOOBt, HNSA, 2-hydroxy pyridine, 3-hydroxy pyridine, 3,4-dihydro-4-oxobenzotriazin-3-ol, 4-hydroxy-2,5-diphenyl-3(2H)-thiophenone-1,1-dioxide, 3-phenyl-1-(p-nitrophenyl)-2-pyrazolin-5-one), [1-benzotriazolyl-N-oxy-tris(dimethylamino)-phosphoniumhexafluorophosphate](BOP), [1-benzotriazolyloxytri-pyrrolidinophosphonium-hexafluoro-phosphate (PyBOP), [O-(benzotriazol-1-yl)-N,N,N',N'-tetramethyluroniumhexafluorophosphate (HBTU), [O-(benzotriazol-1-yl)-N,N,N',N'-tetramethyluronium-tetrafluoroborate (TBTU), [O-(benzotriazol-1-yl)-N,N,N',N'-bis(pentamethylen)uronium-hexafluorophosphate, [O-(benzotriazol-1-yl)-N,N,N',N'-bis(tetramethylen)uronium-hexafluorophosphate, carbonyldiimidazole (CDI), carbodiimides, examples are 1-(3-dimethylaminopropyl)-3-ethylcarbodiimide (EDC), dicyclohexylcarbodiimide (DCC), diisopropylcarbodiimide (DIPC).

When the process of the invention results in the formation of an imine, it is preferred that the process further comprises the step of reducing the imine to a secondary amine.

This is preferably achieved in a single step selective reduction, more preferably by a selective reducing agent selected from the group consisting of:

sodium cyano boro hydride, sodium boro hydride, 4-(dimethylamino)pyridin-borocomplex, N-ethyldiisopropylamine-borocomplex, N-ethylmorpholine-borocomplex, N-methyl-morpholine-borocomplex, N-phenylmorpholine-borocomplex, lutidin-boro-complex, triethylamine-boro-complex, trimethyl-amine-borocomplex; sodium triacetate-borohydride, sodium triethyl-borohydride, sodium trimethoxyboro-hydride, potassium tri-sec-butylborohydride (K-selectride), sodium-tri-sec-butylborohydride (N-selectride), lithium-tri-sec-butylborohydride (L-selectride), potassium triamylborohydride (KS-selectride) und lithium-tri-amylborohydride (LS-selectride), most preferably by sodium cyano boro hydride.

It is especially preferred that the imine is reduced by $NaBH_3CN$ at pH values of 6-7.

The functional group involved in the coupling reaction of the process of the present invention can be the aldehyde functional group of one or more saccharide units, preferably one or more terminal saccharide units in the oligosaccharide S. This aldehyde, functional group can be used as such or be further chemically modified.

In a preferred embodiment the process of the invention further comprises a step b') or c') prior to step b) or c), respectively, wherein one or more terminal aldehyde group(s) of an oligosaccharide S precursor are selectively oxidized to produce the oligosaccharide S to be used in step b) or c).

Preferred oxidation steps for oxidizing one or more terminal aldehyde group(s) of oligosaccharide S to carboxylic or activated carboxylic group(s) are those using (i) halogen, preferably $I_2$, $Br_2$, in alkaline solution, or
(ii) metal ions, preferably $Cu^{++}$ or $Ag^+$, in alkaline solution, or
(iii) electrochemical oxidation.

The resulting carboxylic group can be used in the coupling reaction to yield an ester, thioester or an amide. The carboxyl group can be used as such or after a previous activation step, that yields an activated carboxylic acid group, such as, e.g. a lactone, an active ester, a symmetric anhydride, a mixed anhydride, a halogenide of a carboxylic acid or any other activated form of a carboxylic group that is suitable to produce the desired ester, thioester or amide bond.

Preferred is a process of the invention, wherein in step c) the one or more activated carboxylic group(s) of an oligosaccharide S are activated carboxylic group(s) selected from the group consisting of a lactone, an anhydride, a mixed anhydride, and a halogenide of a carboxylic acid.

Preferably, the process of the invention is one, wherein in step c) the one or more activated carboxylic group(s) of an oligosaccharide S is (are) a lactone group(s).

Preferably such a lactone group results from the oxidation of a terminal aldehyde group of an aldose. More preferably, the oxidation is performed with $I_2$ in the presence of NaOH, yielding a carboxylic intermediate group that is transformed into a lactone by water elimination.

With the process of the invention such as the one described in an exemplary fashion in example 1 it is possible to reach almost quantitative yields.

The oligosaccharide lactone derivative is sufficiently active to react with a primary amino function. In contrast to the normal conditions that are used for similar coupling reactions, that usually require the presence of activators, e.g., carbodiimides, it was surprisingly found that the reaction also proceeds readily with high chemical yields without an activator. This is a substantial advantage in that additional purification steps that are necessary for separating the activator and its by-products are redundant.

Preferably, the coupling of a lactone oligosaccharide derivative and one or more pharmaceutically active compound(s) X comprising an amino function is performed in the absence of an activator.

Due to the low stability in water of such lactones and due to the low water solubility of the pharmaceutically active component the reaction is preferably performed in presence of a suitable organic solvent.

Preferred organic solvents are polar non-protic ones (DMF, DMSO, N-methylpyrrolidone and the like) or lower alcohols (i.e. $C_{1-10}$, e.g MeOH, EtOH, PrOH, i-PrOH, n-butanol, iso-butanol, tert-butanol, glycol, glycerol). In specific cases it may also be of advantage to perform the reaction in a heterogeneous liquid phase, e.g. a liquid dispersion or suspension.

The functional groups involved in the coupling of X and S can be a nucleophilic group selected from an alcohol, thiol, and amine functional group and an acceptor functional group, selected from an aldehyde, carboxylic acid, and an activated carboxylic acid functional group, preferably a lactone. Any of the functional groups may be naturally present on a component X or S or may be introduced by chemical transformation, e.g. reductive amination of an oligosaccharide by reacting it with, e.g. a diamine (i.e. hydrazine, DAB or homologues thereof) to yield an amino function).

Another way of transforming and linking functional groups is by means of introducing a bifunctional linker that comprises at least two functional groups that are compatible with the selected components X and S.

In a further aspect the present invention relates to a process for preparing compounds according to the invention, comprising the steps of:
a) coupling a suitable bifunctional linker group(s) to compound X, and
b) coupling the product(s) of step a) with one or more aldehyde, carboxylic acid, or activated carboxylic group(s) of an oligosaccharide S, or
a') coupling a suitable bifunctional linker group(s) to one or more aldehyde, carboxylic acid, or activated carboxylic group(s) of a oligosaccharide S, and
b') coupling the product(s) of step a) with one or more compound(s) X.

When an imine bond is formed between the bifunctional linker group and the component X and/or S it may preferably be further reduced to a secondary amine. Preferably this is achieved in a single step selective reduction, more preferably by a selective reducing agent selected from the group consisting of:

sodium cyano boro hydride, sodium boro hydride, 4-(dimethylamino)pyridin-borocomplex, N-ethyldiisopropylamine-borocomplex, N-ethylmorpholine-borocomplex, N-methyl-morpholine-borocomplex, N-phenylmorpholine-borocomplex, lutidin-boro-complex, triethylamine-boro-complex, trimethyl-amine-borocomplex; sodium triacetate-borohydride, sodium triethyl-borohydride, sodium trimethoxyboro-hydride, potassium tri-sec-butylborohydride (K-selectride), sodium-tri-sec-butylborohydride (N-selectride), lithium-tri-sec-butylborohydride (L-selectride), potassium triamylborohydride (KS-selectride) und lithium-triamylborohydride (LS-selectride), most preferably by sodium cyano boro hydride.

It is especially preferred that the imine is reduced by $NaBH_3CN$ at a pH values of 6-7.

It is also preferred that in step b) or step a') the one or more activated carboxylic group(s) of an oligosaccharide S are activated carboxylic group(s) selected from the group consisting of a lactone, an anhydride, a mixed anhydride, and a halogenide of a carboxylic acid.

Suitable linker molecules are those that have at one end any reactive functional group that reacts with the component X and at the other end any reactive functional group that is able to react with an oligosaccharide S. Preferably, said bifunctional linker reacts with an amine, alcohol, thiol, aldehyde, carboxylic acid, or activated carboxylic acid of X and S.

Many suitable linkers are known in the art. Preferably, the suitable linkers form an amide, imine, secondary amine, ester, thioester, urea, carbonate, and/or carbamate bond In a preferred embodiment, the bifunctional linker is preferably non-toxic and physiologically acceptable. More preferably, the bifunctional linker comprises a linear or branched aliphatic chain, preferably an aliphatic chain of 1 to 20, more preferably 1 to 12, most preferably 2 to 6 carbon atoms.

Particularly preferred bifunctional linkers are selected from the group consisting of:

a) linker molecules that connect an —SH group with an amino group, preferably derived from a compound selected from the group consisting of:
AMAS (N-α(Maleimidoacetoxy)succinimide ester),
BMPS (N-β(Maleimidopropyloxy)succinimide ester),
GMBS (N-γ(Maleimidobutyryloxy)succinimide ester),
EMCS (N-ε(Maleimidocaproyloxy)succinimide ester),
MBS (m-Maleimidobenzoyl-N-hydroxysuccinimide ester),
SMCC (Succinimidyl4-(N-maleimidomethyl)-cyclohexane-1-carboxylate),
SMPB (Succinimidyl-4-(p-maleimidophenyl)butyrate),
SPDP (Succinimidyl-3-(2-pyridyldithio)propionate),
Sulfo-GMBS (N-(γ-Maleimidobutyryloxy)sulfosuccinimide ester), and
Sulfo-EMCS (N-(ε-Maleimidocaproyloxy)sulfosuccinimide ester);
b) linker molecules that connect two —SH groups, preferably derived from a compound selected from the group consisting of:
BMB (1,4-Bis-maleimidobutane),
BMDB (1,4-Bis-maleimido-2,3-dihydroxybutane),
BMH (Bis-maleimidohexane),
BMOE (Bis-maleimidoethane),
DTME (Dithio-bis-maleimidoethane),
HBVS (1,6-Hexane-bis-vinylsulfone),
$BM(PEO)_3$ (1,8-Bis-maleimidotriethyleneglycol), and
$BM(PEO)_4$ (1,11-Bis-maleimidotetraethyleneglycol);
c) linker molecules that connect two amino groups, preferably derived from a compound selected from the group consisting of:
BSOCOES (Bis-(2-(succinimidyloxycarbonyloxy)-ethyl)sulfone,
$BS^3$ (Bis-(sulfosuccinimidyl)suberateDFDNB (1,5-Difluoro-2,4-dinitrobenzene),
DMA (Dimethyladipimidate 2 HCl),
DSG (Disuccinimidyl glutarate),
DSS (Disuccinimidyl suberate), and
EGS (Ethylene glycol bis(succinimidylsuccinate),
d) linker molecules that connect an —SH group and a —CHO functional groug, preferably derived from a compound selected from the group consisting of:
BMPH (N-(β-Maleimidopropionic acid)hydrazide TFA),
EMCH (N-(ε-Maleimidocaproic acid)hydrazide),
KMUH (N-(κ-Maleimidoundecanoic acid)hydrazide),
$M_2C_2H$ (4-(N-Maleimidomethyl)cyclohexane-1-carboxylhydrazide HCl),
MPBH (4-(4-N-Maleimidophenyl)butyric acid hydrazide HCl), and
PDPH (3-(2-Pyridyldithio)propionyl hydrazide),
e) linker molecules that connect an —SH group to an —OH group, preferably a compound derived from PMPI (N-(p-Maleimidophenyl)isocyanate);
f) linker molecules that connect an —SH group to a —COOH group, preferably derived from a compound selected from the group consisting of:
BMPA (N-β-Maleimidopropionic acid),
EMCA (N-ε-Maleimidocaproic acid), and
KMUA (N-κ-Maleimidoundecanoic acid);
g) linker molecules that transform an amino group into a carboxyl group, preferably derived from a compound selected from the group consisting of: MSA (Methyl-N-succinimidyladipate) and its longer and shorter chain homologues or the corresponding ethylene glycol derivatives;

h) linker molecules that transform a —COOH group into an amino group, preferably derived from a compound selected from the group consisting of: DAB (1,4-Diaminobutane) or its longer and shorter chain homologues or the corresponding ethylene glycol derivatives.

The direct (by amide, ester, imine, secondary amine, carbonate, carbamate, urea, or thioester bond) or indirect (by bifunctional linker molecules) coupling products can be analyzed by standard chromatographic methods (such as, e.g., HPLC, TLC) and be fully characterized using MS, IR or NMR. This is a substantial advantage versus polymer conjugation. The reaction product of the oligosaccharides is clearly defined because it is a unique entity and not the sum of many polydisperse homologues as they are in the field of polymer conjugation. Thereafter, purification, isolation and characterisation techniques become more effective when working with the oligosaccharide conjugates of the present invention.

Component X is that part of the conjugates according to the invention that mediates its pharmaceutical utility. Therefore, conjugates of the present invention will be pharmaceutically active, too, and in addition provide the advantages over the pharmaceutically active component alone that have been described in more detail above.

Thus, in a further aspect the present invention relates to compound according to the invention for use as a medicament.

In addition, the present invention relates to a pharmaceutical composition comprising at least one of the compounds according to the invention and a pharmaceutically acceptable carrier.

It is particularly preferred to formulate the compounds of the invention by freeze-drying. On one side, freeze drying is a preferred dehydration and purification step. On the other side, freeze-drying will enhance the stability of saccharide compositions.

Therefore, the present invention relates to freeze-dried pharmaceutical composition comprising at least one of the compounds according to the invention and a pharmaceutically acceptable carrier.

The dehydrated, in particular freeze-dried pharmaceutical compositions may be regenerated to be ready for use by adding at least one physiologically acceptable aqueous solvent, such as water, physiological saline or any other suitable aqueous formulation.

In this respect, the present invention also relates to a kit comprising at least one of the compounds according to the invention in a dehydrated form, preferably in lyophilized form, and at least one physiologically acceptable aqueous solvent.

In pharmaceutical compositions the molar ratio of oligosaccharide and pharmaceutically active substance is preferably in the range from 20:1 to 1:1, preferably from 5:1 to 1:1.

In general, the compounds of the present invention demonstrate high solubility and stability in aqueous solutions and also in physiological media in vitro. Depending on the therapeutical need the compounds of the present invention can in be designed to be cleaved very rapidly in plasma and esterase solutions, a few of them even quantitatively within a few minutes (e.g. in case of ester bonds) or act as slow release forms of the drug (e.g. when bonded as amide), thus providing excellent prodrugs (i.e. conjugated drugs that display their pharmaceutical effect only after being released in the free form). The compounds of the present invention are also efficacious in vivo. Some acting as prodrugs are readily hydrolyzed in the bloodstream. Others will be hydrolyzed very slowly, thus providing slow release forms of the pharmaceutically active compound. Alternatively even others will retain their pharmaceutical activity while conjugated.

In effecting treatment of a mammal in need of pharmaceutical action, the compounds disclosed by the present invention for said purpose can be administered in any form or mode which makes the therapeutic compound bioavailable in an effective amount, including oral or parenteral routes. For example, products of the present invention can be administered by enteral (oral, sublingual, buccal and rectal), parenteral (intradermal, subcutaneous, intramuscular, intraperitoneal, intravenous, intraarterial, intraarticular, intrathecal and epidural), topical (creams, ointments, lotions, transdermal patches, eye drops, inhalants, vaginal creams, rings and sponges, implants), intranasal, buccal, rectal routes, and the like.

Parenteral administration of the compounds of the present invention is preferred.

One skilled in the art of preparing formulations can readily select the proper form and mode of administration depending upon the particular characteristics of the product selected, the disease or condition to be treated, the stage of the disease or condition, and other relevant circumstances. (Remington's Pharmaceutical Sciences, Mack Publishing Co. (1990)). The products of the present invention can be administered alone or in the form of a pharmaceutical preparation in combination with pharmaceutically acceptable carriers or excipients, the proportion and nature of which are determined by the solubility and chemical properties of the product selected, the chosen route of administration, and standard pharmaceutical practice. Non-limiting examples of acceptable carriers or excipients are, e.g. binders, coatings, fillers, compression and encapsulation aids, disintegrants, creams and lotions, lubricants, materials for chewable tablets, parenterals, plasticizers, powder lubricants, soft gelatin capsules, spheres for coating, spheronization agents, suspending and gelling agents, sweeteners, wet granulation agents. For oral application suitable preparations are in the form of tablets, pills, capsules, powders, lozenges, sachets, cachets, suspensions, emulsions, solutions, drops, juices, syrups, while for parenteral, topical and inhalative application suitable forms are solutions, suspensions, easily reconstitutable dry preparations as well as sprays. Compounds according to the invention in a sustained-release substance, in dissolved form or in a plaster, optionally with the addition of agents promoting penetration of the skin, are suitable percutaneous application preparations. The products of the present invention, while effective themselves, may be formulated and administered in the form of their pharmaceutically acceptable salts, such as acid addition salts or base addition salts, for purposes of stability, modulation of hydrophobicity, increased solubility, and the like.

The amount of active agent to be administered to the patient depends on the molecular weight and toxicity of the drug, the patient's weight, on the type of application, symptoms and the severity of the illness. Normally, 0.1 mg/kg to 25 mg/kg of at least one substance of the present invention is administered but when applied locally, e.g. intracoronary administration, much lower total doses are also possible.

FIGURES

FIG. 1 shows the results of the inhibition test with modified amphotericin B according to example 9. Assay conditions according to DIN 58940. Mlt-AmpB=maltotrionic acid conjugated amphotericin B. Clear wells indicate no growth of the test organism *Candida albicans* (i.e. positive effect of AmpB). Turbid wells indicate growth of the test organism (i.e. no effect of AmpB). MIC=minimal inhibitory concentration The following examples further illustrate the best mode contemplated by the inventors for carrying out their invention. The examples relate to preferred embodiments and are not to be construed to be limiting on the scope of the invention.

EXAMPLE 1

Selective Oxidation of Maltotriose Reducing End

In a round bottom flask one gram of maltotriose (~2 mmol) was dissolved in distilled water (1.0 ml). Thereafter 2.0 ml of a 0.1 N $I_2$ solution were added and the solution became brown. A 2 ml pipette containing 2.0 ml 1 N NaOH solution was then connected to the flask using a two ways connector, and the NaOH solution was dropped in, once every four minutes (each drop having the volume of ~20 µl). After adding almost 0.2 ml of the NaOH the solution started to become clear again, then the second 2 ml portion of 0.1 N $I_2$ solution had to be added. At the end of this process 50 ml a 0.1 N $I_2$ solution and 7.5 ml of 1 N NaOH solution was used.

The reaction was then stopped, acidified with 2.0 N HCl solution, and extracted several times with ethyl ether in order to remove any $I_2$ left. At the end the solution was passed directly through the cation exchanger IR-120 H$^+$, and then incubated overnight in presence of silver carbonate in order to eliminate any excess of iodine/iodide. Thereafter the filtrate was passed once more through the same cation exchanger before being lyophilised. The final yield was found to be 85% and 95%.

EXAMPLE 2

Coupling of Amphotericin B to Maltotrionic Acid 46.61 mg of maltotrionic acid lactone and 21.31 mg of Amphotericin B (ratio ~4:1) were dissolved in 1.0 ml of anhydrous DMSO under inert atmosphere (argon). The temperature was increased up to 70° C. and the reaction was allowed to run protected from light under moderate stirring conditions for 24 h. Thereafter the reaction was stopped by adding 20 ml of cold acetone which precipitates the coupling product. The precipitate was then washed once more with cold acetone, then with methanol and finally again with acetone, before being dissolved in water and lyophilised. The coupled product has a drug content (estimated by UV absorption at 410 nm) of 120 µg per mg.

Analogous reactions have been performed also with Mepartricin and with Nystatin.

EXAMPLE 3

Coupling of Neomycin to Maltotrionic Acid

In a two-necked round bottom flask, 64 mg of Neomycin and 52 mg of maltotrionic acid lacton were dissolved in 2.0 ml DMSO. After increasing the temperature up to 70° C., the reaction ran for 24 h under inert atmosphere (argon). The reaction was finally stopped and the coupling product precipitated by adding cold acetone. The precipitate was washed one more time with methanol and finally again with acetone. After dissolving it in water the product was lyophilized to yield 108 mg of coupling product (yield 93%).

EXAMPLE 4

Coupling of Daunorubicin to Maltotrionic Acid

In a two-necked round bottom flask 0.7 mg of Daunorubicin were dissolved in 1 ml DMSO together with 62.41 mg of maltotrionic acid lacton and 0.152 mg of DMAP. The reaction ran at 70° C., for 24 h under argon atmosphere and moderate stirring. The reaction was stopped by adding cold acetone which precipitates the conjugate. After centrifugation the solid pellet is resuspended in acetone several times until the filtrate did not show any more red coloration. The pellet is finally dissolved in water and lyophilised. The purity of the coupling product was checked by RP-HPLC and the drug content was determined by UV photometry. The coupling product contains 0,4 µg Daunorubicin per mg. The yield was 78%.

EXAMPLE 5

Coupling of Propofol to Lactobionic Acid a) Synthesis of Succinic Acid Mono-Propofol Ester In a 50 ml round bottom flask 1 ml of propofol has been stirred with 2.5 ml of TEA at room temperature. When the mixture looked homogeneous 5.5 mmol of succinnic anhydride were added. The reaction was allowed to proceed under moderate stirring conditions for 22 h. The progress of the reaction was followed by TLC monitoring or by simply observing the disappearance of succinic anhydride whose solubility in the mixture is low, so most of it remained in the reaction vessel as a white solid. After 22 h the reaction was stopped, the solution looked brownish. After elimination of most of the TEA under vacuum, 10 ml of 0.2 N HCl were added to the solution which was vigorously stirred and kept in an ice bath for 30 min. Thereafter the white swaying precipitate was removed from the reaction by filtration through a proper funnel filter. The precipitate was dissolved once more in EtOH and precipitated a second time by adding cold water, filtrated and kept at –20° C.

b) Synthesis of Lactobionic Acid Hydrazide

Three grams of lactobionic acid were dissolved in 5 ml of warm DMSO (~70° C.). After the complete dissolution 7.5 mmol of mono chloride salt of hydrazine were added to the reaction vessel. The solution was stirred at 45° C. for 20 h. The proceeding of the hydrazide formation was monitored using TLC coupled with a ninhydrin test to reveal the presence of free amino groups. The protonated amine appeared yellow in the ninhydrin test. When the reaction seemed complete, it was stopped by adding an excess of water and then 0.1 N NaOH solution was inserted dropwise until a pH ~10 was reached in order to neutralise the HCl. The mixture was frozen and lyophilised. The dry product was then dissolved in water and lyophilised once more to eliminate the last traces of DMSO.

c) Alternative Synthesis of Lactobionic Acid Hydrazide

Three grams of lactobionic acid lactone were dissolved in 5.0 ml of warm DMSO (~70° C.). Once dissolved 1.0 gram of monoBOC-Hydrazine was added to the reaction vessel. The reaction ran for 16 h under inert atmosphere (argon) and was monitored by TLC (eluent $CH_3Cl$). When the spot of the BOC-hydrazine disappeared the reaction was stopped, cooled down to 4-5° C. and extracted with water—chloroform several times. The aqueous phase was finally degassed and lyophilized. The product dissolved in MeOH has been deprotected from the BOC-function by bubbling HCl gas into the solution for 30'. The deprotection was also monitored by TLC. At the end the solvent was completely evaporated, the solid was washed three times with ethyl ether in order to remove completely the remaining HCl and finally dissolved in water and lyophylized. The hydrochloride salt was characterised by ESI-MS.

d) Synthesis of Lactobionic Acid Diamino Butanamide

Three grams of lactobionic acid lacton were dissolved in 3.0 ml of warm DMSO (~70° C.). In a separate vessel a 30 times molar excess of diamino butane was dissolved in 2.0 ml of DMSO and then added to the first solution. The reaction was left under argon overnight under moderate stirring. The monitoring of the reaction was done by TLC. After stopping the reaction by adding 30 ml of NaOH sol. 0.01 N, this solution was extracted with a mixture chloroform/ethyl acetate 4:1 several times. The organic phase, washed two times with water was eliminated, while the aqueous phase, after degassing, was lyophilized. The product showed the calculated mol peak in ESI-MS.

e) Final Coupling

One mmol of the succinic acid mono-propofol ester and one mmol of the lactobionic acid amino derivative (from reaction b, c, or d) were dissolved in 3 ml of DMF and stirred at room temperature. The temperature was decreased to 0° C. and a 1:1 molar amount of DCC was added to the chilled solution. The reaction was allowed to run one hour under these conditions before increasing gradually the temperature to 25° C. The reaction was monitored by TLC coupled with a ninhydrin test. The disappearance of the free amino functions indicated the end of the reaction (normally after 2 h). The reaction was then stopped by adding dilute HCl. The precipitate was washed three times with cold water and then eliminated. The aqueous fractions were frozen and lyophilized. The purity of the product was checked by TLC, confirmed by RP-HPLC ($C_{18}$), and its characterisation was done by ESI-MS.

EXAMPLE 6

Coupling of Propofol to Glucosamine

In a two necked round bottom flask 1.8 mmol of succinic acid mono-propofol ester is dissolved in 2.0 ml of MeOH. The solution is then chilled in an ice bath. A 5 times molar excess of CDI is then added to the solution and allowed to run in the same conditions for 15 min. With the help of a dropping funnel an equimolar solution of glucosamine in 2 ml of MeOH was slowly added during 10 min. Thereafter the reaction was allowed to proceed for one more hour on ice and then overnight at room temperature. The reaction is monitored by TLC. The reaction was finally stopped by adding 10 ml of a cold 0.1 N HCl solution, filtered and passed through a cation exchanger column filled with IR-120 $H^+$. The eluate is finally lyophilised and the purity is checked by RP-HPLC. The product was characterized by ESI-MS and NMR.

EXAMPLE 7

Coupling of Propofol to Maltotrionic Acid

In 2.0 ml of a 3:1 DMSO:MeOH mixture were dissolved 200 mg of Propofol, a three times molar excess of maltotrionic acid, and a catalytic amount of TEA. The solution was left stirring at room temperature for 10 min. In a separate vessel 350 mg of DCC were dissolved in 1 ml of the same solution and added dropwise to the previous mixture during a 3 min. time period. The reaction was warmed up to 60° C. and allowed to run under these conditions for 20 h. Finally it was stopped and then filtrated. The coupling product was recovered by precipitation in acetone (50 ml) and washed several times with EtOH (100 ml), ethyl acetate (100 ml) and finally acetone (100 ml). The reaction has been monitored by TLC and the purity of the product has been confirmed also by RP-HPLC on a C-18 column.

EXAMPLE 8

Coupling of Propofol to Glucuronic Acid

In a two necked 50 ml round bottom flask 10 mmol of glucuronic acid were dissolved in 2.0 ml of DMF. An equimolar amount of TEA was added and the solution was cooled down in an ice bath. Then 12 mmol of isobutyl chlorocarbonate were added and the reaction was kept cold for 30 min. In a separate vessel 10 mmol of propofol were mixed with 0.5 ml of TEA and then added dropwise to the first solution with the help of a dropping funnel. The reaction run for 1 day at 4° C. and overnight at room temperature. It was monitored by TLC. After stopping the run the solution was evaporated yielding a brown oily product which was dissolved in water and extracted several times with chloroform. The organic phase, washed two times with water can be eliminated. The aqueous phase, after degassing, was passed through a mixed ion exchanger before being lyophilised. The purity was checked by RP-HPLC and the product has been characterised by ESI-MS and NMR.

EXAMPLE 9

Coupling of Propofol to Gluconic Acid a) Synthesis of Gluconic Acid Hydrazide

Five grams of gluconic acid were suspended in 15 ml of warm MeOH. After the complete dissolution 4 grams of monoBOC-hydrazine were added to the reaction vessel. The solution was refluxed for 36 h. After the addition of monoBOC-hydrazine the suspension disappeared. At the end, the reaction showed a white precipitate which contained most of the product. The solvent was removed under vacuum and the solid product was extracted in a mixture of NaOH sol. 0.1 N/chloroform. The organic phase was removed while the aqueous phase was passed through anionic exchanger resin and lyophilized. Finally, product was dissolved in cold MeOH and deprotected from the BOC-function by bubbling HCl gas into the solution over 30'. The purity of the protected and the deprotected product was checked by TLC, HPLC and the identity was confirmed by ESI-MS.

b) Final Coupling 1 mmol of the succinic acid mono-propofol ester (from reaction a) of example 5) and 1 mmol of the gluconic acid amino derivative (from reaction b) were dissolved in 3 ml of DMF and stirred at room temperature. Then, a 1.5 molar excess of CDI (1,1'-Carbonyldiimidazole) was added to the reaction vessel together with 150 μl of TEA. The reaction was allowed to proceed overnight under these conditions. The reaction was monitored by TLC coupled with a ninhydrin test. The disappearance of the free amino functions indicated the end of the reaction. The reaction was then stopped and the solvent evaporated under vacuum. The residue, still oily, was purified by flash chromatography on silica gel using a mixture $CHCl_3$/MeOH as eluent. The purity of the final product was checked by TLC, confirmed by RP-HPLC ($C_{18}$), and its characterisation was done by ESI-MS.

EXAMPLE 10

Coupling of Propofol to Modified Glucose a) Synthesis of an Amino Derivative of Glucose 5 g glucose and 3.5 mg monoBOC-Hydrazine were dissolved in 60 ml of a 5:1 MeOH-water mixture in a 250 ml round bottom flask. The solution was briefly warmed to 60° C. (5-10 minutes, optional) and then was allowed to reach room temperature slowly. Thereafter, 2.6 g of $NaBH_3CN$ were added and the pH was corrected to 6-7 by adding a few drops of a 2N HCl solution. The reaction was allowed to run for 12 days while checking and correcting the pH to 6-7 by means of a 2N HCl solution daily. The reaction was considered finished when no shift in the pH value was observed. At the end, the MeOH was evaporated under vacuum and the water solution was extracted with $CHCl_3$ several times. The aqueous phase was then degassed, incubated in the presence of anionic exchanger and lyophilized. Finally, the solid product was dissolved in a 8:2 $CHCl_3$/MeOH mixture and extracted on silica gel. The organic solvents were evaporated, the product was dissolved in water and again lyophilized. 6.56 g purified product, corresponding to a yield of 79% were obtained. The product was characterised by ESI-MS. Part of this product was deprotected from the BOC-function and another part was utilised as such, postponing the deprotection after the final coupling step. In both cases the deprotection was carried out by dissolving the product in cold MeOH and bubbling HCl into this solution for 30'.

b) Final Coupling

Three mmol of the succinic acid mono-propofol ester (from step a) of Example 5) and three mmol of the 1-deoxy-1-hydrazinoglucitol (from reaction b) were dissolved in 10 ml of DMF and stirred at room temperature. Then, a 1.5 molar excess of CDI was added to the reaction vessel together with 150 µl of TEA. The reaction was allowed to run overnight under these conditions. The reaction was monitored by TLC coupled with a ninhydrin test. The disappearance of the free amino functions indicated the end of the reaction. The reaction was then stopped and the solvent was evaporated under vacuum. The residue, still oily, was purified by flash chromatography using a mixture $CHCl_3$/MeOH as eluent on silica gel. The purity of the final product was checked by TLC, confirmed by RP-HPLC ($C_{18}$), and its characterisation was done by ESI-MS.

Also, the same reaction was performed with the BOC-protected 1-deoxy-1-hydrazinoglucitol.

EXAMPLE 11

Determination of Solubility and Antimycotic Activity of Maltotrionic Acid Coupled Amphotericin B (Mlt-AmpB)

In order to show the effectiveness of Amphotericin B after covalent coupling to maltotrionic acid the conjugate was checked by its growth inhibition potential of the pathogen *Candida albicans* according to a standardised procedure (DIN 58940).

Test Method

Bouillon dilution method carried out in 96 well microtitration plates according to E DIN 58940 Medical microbiology—Susceptibility testing of pathogens to antimicrobial agents, Part 84: Microdilution—Special requirements for testing of fungi against antifungal agents. Results are given as MIC (minimal inhibitory concentration). The MIC is the lowest concentration where no visible fungal growth can be detected in the tested sample.

Test Conditions
Strain: *Candida albicans* DSM 11943
Inoculum: *C. albicans* $5*10^4$ KBE/ml in High Resolution Medium (Oxoid)
Incubation Temperature: 30° C.
Sample volume: 100 µl
Test volume: 200 µl (100 µl sample+100 µl inoculum)

Tested Substance/MIC desired value
Tested Substance:
Mit-AmpB, drug content: 2.05 µg per mg.
Amphotericin B from Alpharma, Denmark, Lot 1970005.

After dissolving the freeze-dried coupled product in PBS (Phosphate Buffered Saline) the solution was filtered through a sterile non-pyrogenic filter (Whatman, 13 mm syringe filter, polysulfone, 0.2 µm) and subsequently a MIC test was carried out. The MIC desired value according to DIN 58940 should be between 0.125 and 1.0 µg/ml.

The result (see FIG. 1) shows that the coupled Amphotericin B has partially lost the original activity, nevertheless it still stays in the accepted activity range. It should be to recognized that the conjugate is completely soluble, since no difference can be observed among the sterile filtered and the non filtered material.

Therefore the loss in potency can be easily compensate with the big increase in solubility. In fact, the conjugate presents a solubility in water higher than 800 mg per ml, which results in an amount of drug in solution of almost 100 mg in 1 ml while the water solubility of the Amphotericin as such is around 0.1 mg per ml and only using solution with extreme pH values. In comparison Mlt-AmpB has a 1000 fold improved water solubility.

The invention claimed is:

1. A compound having the formula

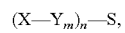

wherein
X is a pharmaceutically active compound,
Y is a bifunctional linker,
S is a mono-, di- or trisaccharide
n is equal or less than the number of the saccharide units in S, and
m is, independently of n, 0 or 1,
and wherein at least one saccharide unit of S is derived from an aldose monosaccharide comprising a free aldehyde group.

2. The compound of claim 1, wherein m=0, and X and S are linked to each other by an amide, imine, secondary or tertiary amine, ether, ester, carbonate, carbamate, urea or thioester bond.

3. The compound of claim 1, wherein m=1, and X and S are linked by means of a pharmaceutical acceptable linking group, said linking group preferably being linked to X and S by an amide, imine, secondary or tertiary amine, ether, ester, carbonate, carbamate, urea or thioester bond and wherein the X—Y bond may be different from the Y—S bond.

4. The compound of claim 1, wherein S is linear and the saccharide units within S are linked by α(1-4) bonds.

5. The compound of claim 1, wherein the viscosity of said compound is 1-100 mPasc.

6. The compound of claim 1, wherein the molar ratio of X to S is in the range of 20:1 to 1:1.

7. The compound of claim 1, wherein S comprises one or more saccharide units selected from the group consisting of:
monosaccharides,
disaccharides, disaccharide homologues,
branched oligosaccharides,
amino monosaccharides, and
modified saccharides.

8. The compound of claim 7, wherein S comprises one or more saccharide selected from the group consisting of glucose, galactose, glucosamine, galactosamine, glucuronic acid, gluconic acid, galacturonic acid, lactose, maltose, maltotriose, isomaltose, isomaltotriose, and neuraminic acid.

9. The compound of claim 1, wherein the pharmaceutical active compound X is selected from the group consisting of:
antibiotic, anti-diabetic, anti-diuretic, anti-cholinergic, anti-arrhythmic, anti-emetic, anti-epileptic, anti-histaminic, anti-mycotic, anti-sympathotonic, anti-thrombotic, androgenic, anti-androgenic, estrogenic, anti-estrogenic, anti-osteoporotic, anti-cancer, immunosuppressing, vasodilatory antipyretic, analgesic, anti-inflammatory drugs, blood pressure lowering drugs, antitussiva, antidepressiva, β-blockers, and vitamins.

10. The compound of claim 1, wherein the pharmaceutically active compound X is selected from the group consisting of:
drugs comprising a primary amino group,
drugs comprising a carboxylic acid group,
drugs comprising an arylic —OH group, and
drugs comprising an aliphatic —OH group.

11. The compound of claim 1, wherein the bifunctional linker is a linker selected from the group consisting of:
linker molecules that connect an —SH group with an amino group,
linker molecules that connect two —SH groups,
linker molecules that connect two amino groups,
linker molecules that connect an —SH group and a —CHO functional group,
linker molecules that connect an —SH group to an —OH group,
linker molecules that connect an —SH group to a —COOH group,
linker molecules that transform an amino group into a carboxyl group, and
linker molecules that transform a —COOH group into an amino group.

12. A process for preparing compounds according to claim 1, comprising the steps of:
a) coupling one or more pharmaceutically active compounds X, comprising an amino, alcohol, and/or thiol group, with one or more aldehyde group(s) of S, or
b) coupling one or more pharmaceutical active compounds X, comprising an amino, alcohol, and/or thiol group with one or more carboxylic group(s) of S, or
c) coupling one or more pharmaceutical active compounds X, comprising an amino, alcohol, and/or thiol group with one or more activated carboxylic group(s) of S, or
d) coupling one or more pharmaceutical active compounds X comprising a carboxyl and/or aldehyde functional group with one or more amino, thiol, or alcohol groups of S.

13. The process of claim 12, wherein the coupling in step a) or d) results in the formation of an imine, further comprising the step of reducing the imine to a secondary amine.

14. The process of claim 12, wherein the imine is reduced by NaBH$_3$CN at pH values of 6-7.

15. The process of claim 12, further comprising a step b') or c') prior to step b) or c), respectively, wherein one or more terminal aldehyde groups of an S precursor are selectively oxidized to produce the S to be used in step b) or c).

16. The process of claim 15, wherein the one or more terminal aldehyde groups of S are selectively oxidized to carboxylic groups or activated carboxylic groups using
halogen,
metal ions, or
(iii) electrochemical oxidation.

17. The process of claim 12, wherein in step c) the one or more activated carboxylic groups of S are activated carboxylic groups selected from the group consisting of a lactone, an anhydride, a mixed anhydride, and a halogenide of a carboxylic acid.

18. The process of claim 12, wherein in step c) the one or more activated carboxylic groups of S are lactone functional groups.

19. The process of claim 17, wherein the coupling of a lactone oligosaccharide derivative and one or more pharmaceutically active compounds X comprising an amino function is performed in the absence of an activator.

20. The process of claim 18, wherein the lactone is coupled in a non-protic solvent or in an alcohol.

21. A process for preparing the compound according to claim 1, comprising the steps of:
a) coupling a suitable bifunctional linker group(s) to compound X, and
b) coupling the product(s) of step a) with one or more aldehyde, carboxylic acid, or activated carboxylic group(s) of S, or
a') coupling a suitable bifunctional linker group(s) to one or more aldehyde, carboxylic acid, or activated carboxylic group(s) of S, and
b') coupling the product(s) of step a) with one or more compound(s) X.

22. The process of claim 21, wherein an imine bond that is formed between the bifunctional linker group and the component X and/or S is further reduced to a secondary amine.

23. The process of claim 22, wherein the imine is reduced by NaBH$_3$CN at pH values of 6-7.

24. The process of claim 21, wherein in step b) or step a') the one or more activated carboxylic groups of S are activated carboxylic groups selected from the group consisting of a lactone, an anhydride, a mixed anhydride, and a halogenide of a carboxylic acid.

25. The process of claim 21, wherein the bifunctional linker comprises a linear or branched aliphatic chain of 1 to 20 carbon atoms.

26. The process of claim 21, wherein the bifunctional linker is selected from the group consisting of:
linker molecules that connect an —SH group with an amino group,
linker molecules that connect two —SH groups,
linker molecules that connect two amino groups,
linker molecules that connect an —SH group and a —CHO functional group,
linker molecules that connect an —SH group to a —OH group,
linker molecules that connect an —SH group to a —COOH group,
linker molecules that transform an amino group into a carboxyl group, and
linker molecules that transform a —COOH group into an amino group.

27. A pharmaceutical composition comprising the compound of claim 1 and a pharmaceutically active carrier.

28. The pharmaceutical composition of claim 27, wherein said composition is freeze-dried.

29. A kit comprising the compound of claim 1 in a dehydrated form or lyophilized form, and at least one physiologically acceptable aqueous solvent.

30. The compound of claim 5, wherein the viscosity of said compound is 1-10 mPasc.

31. The compound of claim 5, wherein the viscosity of said compound 1-7 mPasc.

32. The compound of claim 6, wherein the molar ratio of X to S is in the range of 15:1 to 1:1.

33. The compound of claim 6, wherein the molar ratio of X to S is in the range of 5:1 to 1:1.

34. The compound of claim 6, wherein the molar ratio of X to S is about 1:1.

35. The compound of claim 7, wherein the one or more saccharide units are selected from the group consisting of ribose, arabinose, xylose, lyxose, allose, altrose, glucose, mannose, gulose, idose, galactose, talose, fucose, lactose, maltose, isomaltose, cellobiose, gentiobiose, melibiose, primeverose, rutinose, maltotriose, isomaltotriose, lactotriose, glucuronic acid, galacturonic acid, panose, isopanose, galactosamine, glucosamine, mannosamine, fucosamine, quinovosamine, neuraminic acid, muramic acid, lactosediamine, acosamine, bacillosamine, daunosamine, desosamine, forosamine, garosamine, kanosamine, kansosamine, mycaminose, mycosamine, perosamine, pneumosamine, purpurosamine, rhodosamine, abequose, amicetose, arcanose, ascarylose, boivinose, chacotriose, chalcose, cladinose, colitose, cymarose, 2-deoxyribose, 2-deoxyglucose, diginose, digitalose, digitoxose, evalose, evemitrose, hamamelose, manninotriose, melibiose, mycarose, mycinose, nigerose, noviose, oleandrose, paratose, rhodinose, rutinose, sarmentose, sedoheptulose, solatriose, sophorose, streptose, turanose, and tyvelose.

36. The compound of claim 10, wherein the pharmaceutically active compound X is selected from the group consisting of Albuterol, Alendronat, Amikazin, Ampicillin, Amoxicillin, Amphotericin B, Atenolol, Azathioprin, Cefaclor, Cefadroxil, Cefotaxim, Ceftazidim, Ceftriaxon, Cilastatin, Cimetidin, Ciprofloxacin, Clonidin, Colistin, Cosyntropin, Cycloserin, Daunorubicin, Doxorubicin, Desmopressin, Dihydroergotamin, Dobutamin, Dopamin, Ephedrin, Epinephrin, ε-Aminocaproic acid, Ergometrin, Esmolol, Famotidin, Flecainid, Folic acid, Flucytosin, Furosemid, Ganciclovir, Gentamicin, Glucagon, Hydrazalin, Imipenem, Isoproterenol, Ketamin, Liothyronin, Merpatricin, Metaraminol, Methyldopa, Metoclopramid, Metoprolol, Mexiletin, Mitomycin, Neomicin, Netilmicin, Nimodipin, Nystatin, Octreotid, Oxytocin, Pamidronat, Pentamidin, Phentolamin, Phenylephrin, Procainamid, Procain, Propranolol, Ritodrin, Sotalol, Teicoplanin, Terbutalin, Thiamin, Tiludronat, Tolazolin, Trimethoprim, Tromethamin, Vancomycin, Vasopressin, Vinblastin, Acetylcystein, Azlocillin, Aztreonam, Benzylpenicillin, Camptothecin, Cefamandol, Cefazolin, Cefepim, Cefotetan, Cefoxitin, Cephalothin, Clavulinic acid, Dicloxacillin, Floxacillin, Folinsäure, Fusidin, Indomethacin, Ketorolac, Melphalan, Piperacillin, Prostacyclin, Prostaglandine, Ticarcillin, Allopurinol, Apomorphin, Doxycyclin, Edrophonium, Minocyclin, Pentazocin, Phentolamin, Propofol, Rifamycine, Tetracyclin, Cyclosporin, Taxol, and Paclitaxel.

37. The compound of claim 11, wherein the bifunctional linker is derived from a compound selected from the group consisting of: N-α(Maleimidoacetoxy)succinimide ester, N-β(Maleimidopropyloxy)succinimide ester, N-γ(Maleimidobutyryloxy)succinimide ester, N-ε(Maleimidocaproyloxy)succinimide ester, m-Maleimidobenzoyl-N-hydroxysuccinimide ester, Succinimidyl-4-(N-maleimidomethyl)cyclohexane-1-carboxylate, Succinimidyl-4-(p-maleimidophenyl)butyrate, Succinimidyl-3-(2-pyridyldithio)propionate, (N-(γ-Maleimidobutyryloxy)sulfosuccinimide ester, N-(ε-Maleimidocaproyloxy)sulfosuccinimide ester, 1,4-Bis-maleimidobutane, 1,4-Bis-maleimido-2,3-dihydroxybutane, Bis-maleimidohexane, Bis-maleimidoethane, Dithio-bis-maleimidoethane, 1,6-Hexane-bis-vinylsulfone, 1,8-Bis-maleimidotriethyleneglycol, 1,11-Bis-maleimidotetraethyleneglycol, Bis-(2-(succinimidyloxycarbonyloxy)-ethyl)sulfone, Bis-(sulfosuccinimidyl)suberate DFDNB (1,5-Difluoro-2,4-dinitrobenzene, Dimethyladipimidate 2HCl, Disuccinimidyl glutarate, Disuccinimidyl suberate, Ethylene glycol bis(succinimidylsuccinate), N-(β-Maleimidopropionic acid)hydrazide TFA, N-(ε-Maleimidocaproic acid)hydrazide, N-(κ-Maleimidoundecanoic acid)hydrazide, 4-(N-Maleimidomethyl)cyclohexane-1-carboxylhydrazide HCl, 4-(4-N-Maleimidophenyl)butyric acid hydrazide HCl, 3-(2-Pyridyldithio)propionyl hydrazide, N-(p-Maleimidophenyl)isocyanate, N-β-Maleimidopropionic acid, N-ε-Maleimidocaproic acid, N-ε-Maleimidoundecanoic acid, Methyl-N-succinimidyladipate and its longer and shorter chain homologues or the corresponding ethylene glycol derivatives; and 1,4-Diaminobutane or its longer and shorter chain homologues or the corresponding ethylene glycol derivatives.

38. The process of claim 16, wherein the one or more terminal aldehyde groups of S are selectively oxidized to carboxylic groups or activated carboxylic groups using $I_2$ or $Br_2$ in alkaline solution, or $Cu^{++}$ or $Ag^+$ in alkaline solution.

39. The process of claim 20, wherein the lactone is coupled in DMF, DMSO, N-methylpyrrolidone, MeOH, EtOH, n-PrOH, i-PrOH, n-butanol, iso-butanol, tert-butanol, glycol, or glycerol.

40. The process of claim 25, wherein the bifunctional linker comprises a linear or branched aliphatic chain of 1 to 12 carbon atoms.

41. The process of claim 25, wherein the bifunctional linker comprises a linear or branched aliphatic chain of 2 to 6 carbon atoms.

42. The process of claim 26, wherein the bifunctional linker is derived from a compound selected from the group consisting of N-α(Maleimidoacetoxy)succinimide ester, N-β(Maleimidopropyloxy)succinimide ester, N-γ(Maleimidobutyryloxy)succinimide ester, N-ε(Maleimidocaproyloxy)succinimide ester, m-Maleimidobenzoyl-N-hydroxysuccinimide ester, Succinimidyl-4-(N-maleimidomethyl)-cyclohexane-1-carboxylate, Succinimidyl-4-(p-maleimidophenyl) butyrate, Succinimidyl-3-(2-pyridyldithio)propionate, N-(γ-Maleimidobutyryloxy)sulfosuccinimide ester), N-(ε-Maleimidocaproyloxy) sulfosuccinimide ester, 1,4-Bis-maleimidobutane, 1,4-Bis-maleimido-2,3-dihydroxybutane, Bis-maleimidohexane, Bis-maleimidoethane, Dithio-bis-maleimidoethane, 1,6-Hexane-bis-vinylsulfone, 1,8-Bis-maleimidotriethyleneglycol, 1,11-Bis-maleimidotetraethyleneglycol, Bis-(2-(succinimidyloxycarbonyloxy)-ethyl)sulfone, Bis-(sulfosuccinimidyl)suberateDFDNB (1,5-Difluoro-2,4-dinitrobenzene, Dimethyladipimidate 2HCl, Disuccinimidyl glutarate, Disuccinimidyl suberate, Ethylene glycol bis(succinimidylsuccinate, N-(β-Maleimidopropionic acid)hydrazideTFA, N-(ε-Maleimidocaproic acid)hydrazide, N-(κ-Maleimidoundecanoic acid)hydrazide, 4-(N-Maleimidomethyl)cyclohexane-1-carboxylhydrazide HCl, 4-(4-N-Maleimidophenyl)butyric acid hydrazide HCl, and 3-(2-Pyridyidithio)propionyl hydrazide, N-(p-Maleimidophenyl)isocyanate, N-β-Maleimidopropionic acid, N-ε-Maleimidocaproic acid, N-κ-Maleimidoundecanoic acid, Methyl-N-succinimidyladipate and its longer and shorter chain homologues or the corresponding ethylene glycol derivatives, and 1,4-Diaminobutane or its longer and shorter chain homologues or the corresponding ethylene glycol derivatives.

* * * * *

UNITED STATES PATENT AND TRADEMARK OFFICE
CERTIFICATE OF CORRECTION

PATENT NO. : 7,538,092 B2 Page 1 of 1
APPLICATION NO. : 10/530849
DATED : May 26, 2009
INVENTOR(S) : Michele Orlando It is certified that error appears in the above-identified patent and that said Letters Patent is hereby corrected as shown below:

Title Page, Foreign Application Priority Data, please delete "202 15 415 U" and insert --202 15 415.7-- therefor;

Column 20, lines 33-34 (Claim 22), please delete "component" and insert --compound-- therefor;

Column 21, line 25 (Claim 35), please delete "evemitrose," and insert --evernitrose,-- therefor;

Column 22, line 15 (Claim 37), please delete "N-ε" and --N-κ-- therefor;

Column 22, line 57 (Claim 42), please delete "Pyridyidithio" and insert --pyridyldithio-- therefor.

Signed and Sealed this

Tenth Day of November, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,538,092 B2 | Page 1 of 1 |
| APPLICATION NO. | : 10/530849 | |
| DATED | : May 26, 2009 | |
| INVENTOR(S) | : Orlando et al. | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 137 days Delete the phrase "by 137 days" and insert -- by 550 days --

Signed and Sealed this

Thirtieth Day of March, 2010

David J. Kappos
*Director of the United States Patent and Trademark Office*